(12) United States Patent
Acland et al.

(10) Patent No.: US 8,119,343 B2
(45) Date of Patent: Feb. 21, 2012

(54) METHOD FOR IDENTIFYING OCULOSKELETAL DYSPLASIA IN DOGS

(75) Inventors: Gregory M. Acland, Kennett Square, PA (US); Orly Goldstein, Ithaca, NY (US); Anna V. Kukekova, Ithaca, NY (US); Jennifer Lynn Johnson, Lansing, NY (US)

(73) Assignee: Cornell University, Ithaca, NY (US)

( * ) Notice: Subject to any disclaimer, the term of this patent is extended or adjusted under 35 U.S.C. 154(b) by 415 days.

(21) Appl. No.: 12/199,137

(22) Filed: Aug. 27, 2008

(65) Prior Publication Data

US 2009/0061448 A1     Mar. 5, 2009

Related U.S. Application Data

(60) Provisional application No. 60/968,150, filed on Aug. 27, 2007.

(51) Int. Cl.
*C07H 21/04* (2006.01)
*C12Q 1/68* (2006.01)

(52) U.S. Cl. ...... 435/6.1; 435/6.11; 435/6.12; 435/91.1; 435/91.2; 536/23.1; 536/24.3

(58) Field of Classification Search ........................ None
See application file for complete search history.

(56) References Cited

U.S. PATENT DOCUMENTS

| 2003/0092019 | A1* | 5/2003 | Meyer et al. | 435/6 |
| 2004/0253606 | A1 | 12/2004 | Aziz et al. | |
| 2006/0051766 | A1 | 3/2006 | Tenmizu et al. | |

OTHER PUBLICATIONS

Goldstein et al. (Mamm Genome, vol. 21, pp. 398-408, 2010).*
Tacher et al. (J. of Heredity, vol. 96, No. 7, pp. 812-816, 2005).*
Lucentini (The Scientist; 2004, vol. 24, p. 20).*
Hirschhorn et al. (Genetics in Medicine. vol. 4, No. 2, pp. 45-61, Mar. 2002).*
Muragaki et al.; A mutation in COL9A2 causes multiple ephiphyseal dysplasia (EDM2); Ann. N.Y. Acad. Sci., Jun. 8, 1996, vol. 785; pp. 303-306; Abstract.
Nakashima et al.; Novel COL9A3 mutation in a family with multiple ephiphyseal dysplasia; Jan. 15, 2005, vol. 132A, No. 2; pp. 181-184; Abstract.
Pellegrini et al.; Cloning and characterization of opticin cDNA: evaluation as a candidate for canine oculo-skeletal dysplasia; Gene, Jan. 9, 2002, vol. 282, No. 1-2; pp. 121-131; Abstract.
Du et al.; Cloning and expression of type II collagen mRNA: evaluation as a candidtae for canine oculo-skeletal dysplasia; Gene, Sep. 19, 2000, vol. 255, No. 2; pp. 307-316; Abstract.
Carrig et al.; Retinal Dysplasia Associated with Skeletal Abnormalities in Labrador Retrievers; JAVMA, Jan. 1, 1977, vol. 170, No. 1; pp. 49-57.
Meyers et al.; Short-limbed dwarfism and ocular defects in teh Samoyed dog; JAVMA, Nov. 1, 1983, vol. 183, No. 9; pp. 975-979.
Warman et al.; The Genese Encoding alpha2(IX) Collagen (COL9A2) Map to Human Chromosome 1p32.3-p33 and Mouse Chromosome 4; Genomics, 1994, vol. 23; pp. 158-162.
Carrig et al.; Inheritance of associated ocular and skeletal dysplasia in Labrador Retrievers; JAVMA, Nov. 15, 1988, vol. 193, No. 10; pp. 1269-1272.
Nelson et al.; Multifocal Retinal Dysplasia in Field Trial Labrador Retrievers; Journal of the American Animal Hospital Association, May/Jun. 1983, vol. 19; pp. 388-392.
Du F, et al., "Search for candidate gene causing oculo-skeletal dysplasia in canine model" IOVS, vol. 40, No. 4, Mar. 15, 1999, p. S474, & Annual Meeting of the Association for Research in Vision and Ophthalmology; May 9-14, 1999.
Du F, et al., "Molecular genetic analysis of oculo-skeletal dysplasia in dogs"IOVS, vol. 41, No. 4, Mar. 15, 2000, p. S204, & Annual Meeting of the Association in Vision and Opthalmology.; Apr. 30-May 5, 2000.
Saig K G et al., "Assessment of collagen genes involved in fragmented medial coronoid process development in Labrador Retrievers as determined by affected sibling-pair analysis" American Journal of Veterinary Research, vol. 67, No. 10, 2006, pp. 1713-1718.

* cited by examiner

*Primary Examiner* — Jeanine A Goldberg
(74) *Attorney, Agent, or Firm* — Hodgson Russ LLP

(57) ABSTRACT

Provided are methods for identifying dogs as likely to be genetically normal, carriers of, or affected with Oculo-skeletal dysplasia (OSD) by determining the presence or absence of a drd2 COL9A2 mutation and/or a drd1 COL9A3 mutation. Also provided is a method for selective breeding of dogs and kits useful for carrying out the methods of the invention.

17 Claims, 8 Drawing Sheets

Figure 1. *(SEQ ID NO:1)*

```
   1 cctgtcagct tacttcctat aaactccaaa ttcctcctcg gtccattagg cagagcaatc
  61 aaattctccc aaattcagct ccaggaacac ctctcaaagc ccagggccct ttgctcacaa
 121 tgccacgcgg ggttggactt tcccaggctc cagaggggtt tctcctggac tattttagct
 181 gaccttgtgg attttctccc ccatgctggg cacaggactg gtaaacaaag tatattctcc
 241 ataaatcata atgaaagctg aaatttatga agccctact acttcatatg aagtacttag
 301 catcatctca ttcaatcttc acaaaaattc tataagatag gattattatt atccccttt
 361 acagaggagg acactatatg gtttcaggtg cctgtggtca ccgttagcga cagattccaa
 421 agcacttcac caacattgct taagggaagg aaaagggagc taagagactg ggagaggggt
 481 gatgctggac aaacgggggga gggggagtgc ttcatggagg aggtcacccc gagggatacc
 541 tagagactct ggtgcttcaa gaagctgcag tgaagaaaag gcaaggtgag gagaaggggg
 601 aggaggagga ggaggaagag gaggaggtgg aggaggagga ggaggacgct ggacggtggg
 661 ggcctgggca gggaggcttc aaggagagca tggccaaggg cggctccagg agcaacagga
 721 gcttcagtgc ttccgggggc actaagaggg cctgggggctc gctggtggcc tccaaaagcc
 781 tgacctccta gctgcggcgg gagcagggag gtgagaggga gatgagggg tctggaggtg
 841 cggcacgggg tgcatggggg ggctcccggg accgccgacc cgtaaggctt gtggtaggct
 901 ttcctgcaga agaggcctgc cggtctgtgc tgctaagcca ggtgggtggg ggcctctgcg
 961 aactgggtg caggacccgg gcggtggggg cctctgcgac ctggggtgca ggacccacgg
1021 ctcgctctcg gcctgcgccc tggagcagag gagcgacggg ccgaggctcg gcccggggtc
1081 aggctgcagg ggccccccg acggccggcg cctcccctcg ggggcagagg gtgggcgctg
1141 gctgcggcgc cgggcggggc ggagctgcgc gggcctcggc ccctcggccg ccctctcggg
1201 tgacggcccc gcggccccg ccccgccccg ccgcatattc aggcgcccgc ccgcccgccc
1261 cgtccgagag cagcccgcgc cgcccgcccg cccgagcctc cgccgccgc ATGGCCGCCG
1321 CCCGCCGCCT CCTGCTGCTG CTCCAGGGGC TCGCGCTCGC CCTGGCGCAG ATCgtaagtg
1381 ccgcggccgc cgcgcggggt cggggtgcgg ggggcggggg cggggacggg tcggggtgcg
1441 ggcctcggcg cttcccctcg gcggggcgca cagcgggcgc gtccgggcgc cgcgagggag
1501 gcggaggggc ccggggagcc aggggggccc tgtccggagg cgcgcggccc ggcctgggac
1561 aggcggcgcg gccgggagcc ccgagagccc gggtggcggg cgagacaatg gtgcccattc
1621 acggggctcc ggtgcccsgg cgccgcctcc ccccgggggg ctccagccag acgccgctcg
1681 gccccgctgc cggggccac cggggcgcgg gacccaccg ggaccggccc gggcgccaag
1741 cctggcacct cgctgcgcgg agggcgcggg ccggggcgg ggggggggc tgcccgcgg
1801 agggcaagcc aacgggaaac ggagggggctc cggggagggg cgcccccgc gtgctcctt
1861 cgggttaggc gcgccaggcg caggggggcag ggcaccgct caccgtcggt acctgtcgtg
1921 cgagcgagcg gtcccggagc ccgccgtcgc ctgcccgctg ggaccgcgg cgcccgctc
1981 tcccgctccg tccaccgccc tccgccctcc gccctccgcc ctccgcgacc gcgcacgggc
2041 cccgcgggcc agcgcaccgg gacgcgctcc gcgctcgctc tccggagcc gggtccccc
2101 gcggccaacc cggggccgcg cctcgggtcc tgagcgccgg gaggggcacc cagggcgccg
2161 cacagtcggt tccccgtgag cgcgccgcgc ccgggggggg ctctccgcag ggaccccgc
2221 ccctgcacc gtctgagggc ctcccctgt gtgtgttctc agAGAGGTCC GCCCGGAGAA
2281 CCGGGGCCCC CGGGCCCCCC GGGGCCGCCG GGAGTGCCTG GATCCGACGG CATCGACgt
```

Figure 2. *(SEQ ID NO:2)* catctctccctcactccctcctcctgtcagcttacttcctataaactccaaattcctcctcggtccatta
ggcagagcaatcaaattctcccaaattcagctccaggaacacctctcaaagcccagggccctttgctcac
aatgccacgcggggttggactttcccaggctccagaggggtttctcctggactattttagctgaccttgt
ggattttctccccccatgctgggcacaggactggtaaacaaagtatattctccataaatcataatgaaagc
tgaaatttatgaagcccctactacttcatatgaagtacttagcatcatctcattcaatcttcacaaaaat
tctataagataggattattattatcccctttttacagaggaggacactatatggtttcaggtgcctgtggt
caccgttagcgacagattccaaagcacttcaccaacattgcttaagggaaggaaaagggagctaagagac
tgggagaggggtgatgctggacaaacggggagggggagtgcttcatggaggaggtcaccccgagggata
cctagagactctggtgcttcaagaagctgcagtgaagaaaaggcaaggtgaggagaaggggggaggaggag
gaggaggaagaggaggaggtggaggaggaggaggaggacgctggacggtgggggcctgggcagggaggct
tcaaggagagcatggccaagggcggctccaggagcaacaggagcttcagtgcttccgggggcactaagag
ggcctggggctcgctggtggcctccaaaagcctgacctcctagctgcggcgggagcagggaggtgagagg
gagatgaggggtctggaggtgcggcacggggtgcatgggggggctcccgggaccgccgacccgtaaggc
ttgtggtaggctttcctgcagaagaggcctgccggtctgtgctgctaagccaggtgggtgggggcctctg
cgaactggggtgcaggacccgggcggtggggcctctgcgacctggggtgcaggacccacggctcgctct
cggcctgcgccctggagcagaggagcgacgggccgaggctcggcccggggtcaggctgcaggggcccccc
cgacggccggcgcctcccctcggggcagagggtgggcgctggctgcggcgccgggcggggcggagctgc
gcgggcctcggcccctcggccgccctctcgggtgacggcccgcggccccgccccgccccgccgcatat
tcaggcgcccgcccgcccgccccgtccgagagcagcccgcgccgcccgcccgccgagcctccgccgccc
gcATGGCCGCCGCCCGCCGCCTCCTGCTGCTGCTCCAGGGGCTCGCGCTCGCCCTGGCGCAGATCgtaag
tgccgcggccgccgcgcggggtcggggtgcgggggggcggggcggggacgggtcggggtgcgggcctcgg
cgcttcccctcggcggggcgcacagcgggcgcgtccggcgccgcgagggaggcggaggggcccggggag
ccagggggccctgtccggaggcgcgcggccggcctgggacaggcggcgcggccgggagccccgagagc
ccgggtggcgggcgagacaatggtgcccattcac

Figure 3. *(SEQ ID NO:3)* ccgcgccgcccgcccgcccgagcctccgccgcccgc[ATG]GCCGCCGCCCGCCGCCTCCTGCTGCTGCTCCAGGGGCT
CGCGCTCGCCCTGGCGCAGATCAGAGGTCCGCCCGGAGAACCGGGGCCCCCGGGCCCCCGGGGCCGCCGGGAGTGC
CTGGATCCGACGGCATCGACGGTGACAAGGGGYCCCCTGGGAAAGCCGGCCCTCCGGGACTGAAGGGAGAGCCTGG
CAAACCCGGGCCAGATGGGCCTGATGGGAAGCCTGGGATTGATGGTCTAACTGGAGCCAAGGGGGAGCCTGGCCCCA
TGGGGATCCCTGGAGTCAAGGGCCAGCCTGGGCTCCCCGGTCCCCCTGGCCTGCCGGGCCCTGGCTTTGCTGGACCT
CCTGGACCACCTGGACCTGTTGGCCTCCCCGGTGAGATTGGAATCACAGGCCCCAAGGGGGATCCCGGACCAGATGG
GCCATCGGGGCCCCGGGGCCACCTGGCAAACCGGGCCGACCCGGAACCATCCAGGGCCTGGAAGGCAGCGCGGATT
TCTTGTGTCCGACCAACTGTCCGGCAGGGGTGAAAGGCCCCCAGGGCTGCAGGGGGTGAAGGGGCATCCTGGCAAA
CGCGGGGTTCTGGGCGATTCTGGCCGCCAGGGGAAGCCGGGTCCCAAGGGAGATGTGGGTGCCTCTGGAGAGCAAGG
CATCCCTGGACCACCGGGTCCCCAGGGCATCAGGGGCTACCCGGGCATGGAGGGACCCAAAGGAGAGATGGGTCCTC
GTGGGTACAAAGGCATGGTGGGCTCCATTGGTGCTGCCGGGTCACCCGGTGAGGAAGGTCCACGGGGGCCACCGGGC
CGAGCGGGGGAGAAGGGCGATGTGGGTGGCCAAGGTCTCCGAGGACCTCAGGGCATAACAGGCCCGAAGGGAGCAAC
CGGGCCCCCAGGCATCGATGGCAAGGATGGGACCCCAGGCACGCCAGGCATGAAGGGCAGTGCGGGACAGGCAGGGC
GGCCAGGAAACCAAGGCCACCAAGGCCTAGCGGGCGTGCCGGGCCAGCCTGGGACAAAAGGAGGCCCGGGAGACAAG
GGTGAACCAGGCCAGCAGGGCCTCCCTGGATTCTCTGGTCCCCCTGGGAAGGAGGGAGAGCCAGGACCTCAAGGAGA
AATCGGACCCCGAGGCATCATGGGGCAGAAGGGTGACCAGGGTGAGAGGGGGCCGGTGGGGCAGCCAGGCCCTCAGG
GACGGCAGGGCCCCAAGGGGGAGCAGGGCCCCCCCGGAATTCCAGGGCCCCAAGGCTTGCCAGGCATCAAGGGAGAC
AAGGGCTTCCCGGGGAAGACCGGCCCCCGCGGCAGCGTGGGCGACCCGGGGGTGGCCGGCCTCCGGGGAGAGAAAGG
CGAGAAGGGCGAGTCCGGCGAGCCGGGGCCCAAGGGACAGCAAGGAGTCCGCGGAGAAGCCGGCTACCCGGGCCCCA
GCGGGGATGCGGGCGCCCCGGGGGTGCAGGGCTACCCCGGGCCCCCCGGCCCTCGAGGACTGGCGGGAGACCGAGGC
GTGCCCGGACTGCCCGGGACAGGGCGTGGCGGGCCGGGACGCCAGCGACCAGCACATCGTGACCGTGATGATGAA
GATGATGCAAGAGCAACTGGCAGAGGTCGCTGTGAGTGCCAAGCGGGAGGCCCTGGGTGCCATCGGGATGGTGGGTC
CGCCAGGACCCCCGGGCCTCCTGGGTACCCAGGCAAGCAGGGACCTCATGGGCACCCTGGCCCTCGGGGCGTTCCT
GGCATCGTGGGAGCCGTGGGTCAGATTGGCAACACCGGCCCCAAGGGAAAACGTGGAGAGAAGGGTGACCGGGGAGA
GATGGGACGCGGGCACCCCGGGATGCCTGGGCCCCCGGGATCCCAGGGCTCCCGGCCGGCCCGGGCAGGCAATCA
ACGGCAAGGACGGGGCCCGCGGCGCCCCAGGGGCCCCGGGGGAAGCAGGCCGACCGGGTCCGCCGGGCCCCGCGGGG
CTGCCCGGCTTCTGTGAGCCCGCGGCCTGCCTGGCAGCCTCGGCCTACGCCTCTGCGCGCCTCACAGAGCCCGGATC
CATCAAAGGGCCA[TGA]gcaggaggccaggacagagcctggcgggcatcctgggggtgggggggggactagattccag
cggggtggacacgcaccccatccct

Figure 4A. *(SEQ ID NO:5)*

```
ATGGCCGGGGCCCCCACGCTGGCCCTGCTCCTGCTCGCGCGGCTCCTGGCCGCCACCCTGACCG
GGACCGGGGCGCAGAAAGTGGGACCTCAAGGCCCCCCGGTCCCCAAGGGCCACCTGGGAAGCC
GGGCAAGGATGGCATTGATGGAGAAGCTGGGCCTCCCGGTCTGCCCGGGTCCCCGGGACCAACA
GGGGCCCCAGGGAAGCCAGGGAAGCCAGGAGAGGCCGGGCTGCCRGGACTGCCCGGTGTGGACG
GCCTGACGGGGCAGGACGGACCTCCCGGACCCAAGGGCGCACCTGGGGAACRGGGAAGCCTGGG
ACCCCCGGGGCCTCCCGGGTTGGGGGGCAAAGGCCTCCCCGGACCCCCCGGAGAGGCAGGAGAG
AGTGGTGTCCCCGGTGGAATCGGCCTCCGGGGCCCCCCGGGACCCTCTGGACTGCCAGGCCTCC
CCGGCCCCCCGGACCTCCCGGACCCCCCGGTCACCCAGGGGTCCTCCCTGAGGGCGCCACTGA
CCTTCAGTGCCCGGCCATCTGCCCACCAGGCCCCCCGGTCCCCCAGGAATGCCGGGGTTCAAG
GGGCCCACCGGCTACAAAGGAGATCAAGGAGAGGTCGGCAAGGACGGCGAGAAGGGCGATCCTG
GCCCCCTGGGCCCGCTGGCGTCCCTGGCTCTGTGGGGCTGCAGGGGCCTCGGGGACTCCGAGG
TCTGCCCGGGCCGGCTGGGCCCCAGGGGATCGGGGTCCCATCGGATTCCGAGGGCCGCCAGGG
ATCCCAGGAGCCCCGGGAAAGTGGGTGACAGAGGCGAGAGGGGCCCAGAGGGTTTCCGCGGCC
CCAAGGGTGACCTTGGCAGACCCGGCCTCAAGGGAGTCCCCGGGATGGCCGGGCCGGGCGGGGA
GCCGGGAATGCCAGGCAAGGACGGCCGGGATGGCGTGCCGGGACTGGACGGCGAGAAGGGAGAG
GCCGGTCGCAACGGTGCCCCAGGAGAGAAGGGTCCCAACGGGCTGCCGGGCCTCCCGGGTCGAG
CAGGGTCCAAGGGCGAGAAGGGAGAACTGGGCCGAGCTGGAGAGCTGGGGAGGCTGGCCCCTC
GGGAGAGCCTGGCATCCCGGGGACGTTGGCGTGCCTGGGGAGCGTGGTGAGGCTGGCCACAGG
GGCTCGGCGGGGCTCTGGGCCCACAAGGCCCTCCTGGAGCCCCTGGCGTCCGCGGCTTCCAGG
GCCAGAAGGGCAGCATGGGCGACCCCGGCCTGCCGGGTCCCCAGGGCCTCCGAGGTGCCTCAGG
TGACCGGGCCCGGGGGGAGCCGCAGGCCCTAAGGGAGACCAGGGCGTTGCAGGTTCCGACGGC
CTCCCTGGGGACAAAGGAGAGCTGGGTCCCGGTGGCCCGGTCGGACCCAAAGGAGAGGCTGGCA
GTCGAGGGGAGCTGGGCCCCAAGGGCATCCAGGGTCCCAAYGGCACCAGCGGCGTCGAGGGCCT
CCCCGGGCCCGCCCGGCCCCGTGGGCTTCCGGGCGTCCAGGGCGTGCCCGGCATCACCGGGAAA
CCGGGGGTTCCGGGGCGAGAAGCCAGCGAGCAGCACATCCGGGAGCTGTGCGGGGGGATGCTCA
GCGAACAAATCGCGCAGTTGGCCGCTCACCTGAGGAAGCCTCTGGCGCCCGGATCCGCCGGGCG
GCCTGGGCCAGCGGGGCCCCAGGCCCCCGGGGCCCCAGGCTCCATCGGCCACCCCGGTGCC
CGAGGGCCCCTGGATACCGCGGCCCCACCGGAGAGCTGGGGGACCCGGGCCCAGAGGGGCCC
CCGGGGACCGAGGAGACAAAGGCTCCGCRGGCGCGGGTCTGGACGGGCCGGCCGGGGACCAGGG
CCTCCAAGGACCACAAGGCGTGCCTGGCGTTAGCAAAGACGGCCGCGACGGGGCCAACGGCGAG
CCCGGGCCTCCAGGCGATCCTGGCCTCCCCGGTGCTGTGGGTGCTCAGGGGACACCCGGCATCT
GCGACACCTCGGCCTGCCAAGGAGCTGTGATGGGAGGCGGCGGGGAAAAGTCAGGTTCTAGAAG
CTTCTAA
```

Figure 4B. *(SEQ ID NO:4)*

```
ATGGCCGGGGGCCCCCACGCTGGCCCTGCTCCTGCTCGCGCGGCTCCTGGCCGCCACCCTGA
CCGGGACCGGGGCGCAGAAAGTGGGACCTCAAGGCCCCCCGGTCCCCAAGGGCCACCTGGG
AAGCCGGGCAAGGATGGCATTGATGGAGAAGCTGGGCCTCCCGGTCTGCCCGGGTCCCCGGG
ACCAACAGGGGCCCCAGGGAAGCCAGGGAAGCCAGGAGAGGCCGGGCTGCCGGGACTGCCCG
GTGTGGACGGCCTGACGGGCAGGACGGACCTCCCGGACCCAAGGGCGCACCTGGGGAACGG
GGAAGCCTGGGACCCCGGGGCCTCCCGGGTTGGGGGGCAAAGGCCTCCCCGGACCCCCCGG
AGAGGCAGGAGAGAGTGGTGTCCCCGGTGGAATCGGCCTCCGGGGCCCCCCGGGACCCTCTG
GACTGCCAGGCCTCCCCGGCCCCCCGGACCTCCCGGACCCCCCGGTCACCCAGGGGTCCTC
CCTGAGGGCGCCACTGACCTTCAGTGCCCGGCCATCTGCCCACCAGGCCCCCCGGTCCCCC
AGGAATGCCGGGGTTCAAGGGGCCCACCGGCTACAAAGGAGATCAAGGAGAGGTCGGCAAGG
ACGGCGAGAAGGGCGATCCTGGCCCCCCTGGGCCCGCTGGCGTCCCTGGCTCTGTGGGGCTG
CAGGGGCCTCGGGGACTCCGAGGTCTGCCCGGGCCGGCTGGGCCCCAGGGGATCGGGGTCC
CATCGGATTCCGAGGGCCGCCAGGGATCCCAGGAGCCCCCGGGAAAGTGGGTGACAGAGGCG
AGAGGGGCCCAGAGGGTTTCCGCGGCCCCAAGGGTGACCTTGGCAGACCCGGCCTCAAGGGA
GTCCCCGGGATGGCCGGGCCGGGCGGGGAGCCGGGAATGCCAGGCAAGGACGGCCGGGATGG
CGTGCCGGGACTGGACGGCGAGAAGGGAGAGGCCGGTCGCAACGGTGCCCCAGGAGAGAAGG
GTCCCAACGGGCTGCCGGGCCTCCCGGGTCGAGCAGGGTCCAAGGGCGAGAAGGGAGAACTG
GGCCGAGCTGGAGAGCTGGGGGAGGCTGGCCCCTCGGGAGAGCCTGGCATCCCGGGGGACGT
TGGCGTGCCTGGGGAGCGTGGTGAGGCTGGCCACAGGGGCTCGGCGGGGCTCTGGGCCCAC
AAGGCCCTCCTGGAGCCCCTGGCGTCCGCGGCTTCCAGGGCCAGAAGGGCAGCATGGGCGAC
CCCGGCCTGCCGGGTCCCCAGGGCCTCCGAGGTGCCTCAGGTGACGGGGCCCGGGGGGAGC
CGCAGGCCCTAAGGGAGACCAGGGCGTTGCAGGTTCCGACGGCCTCCCTGGGGACAAAGGAG
AGCTGGGTCCCGGTGGCCCGGTCGGACCCAAAGGAGAGGCTGGCAGTCGAGGGGAGCTGGGC
CCCAAGGGCATCCAGGGTCCCAATGGCACCAGCGGCGTCGAGGGCCTCCCGGGCCCGCCCGG
CCCCGTGGGCTTCCCGGGCGTCCAGGGCGTGCCCGGCATCACCGGGAAACCGGGGGTTCCGG
GGCGAGAAGCCAGCGAGCAGCACATCCGGGAGCTGTGCGGGGGGATGCTCAGCGAACAAATC
GCGCAGTTGGCCGCTCACCTGAGGAAGCCTCTGGCGCCCGGATCCGCCGGGCGGCCTGGGCC
AGCGGGGCCCCAGGCCCCCGGGGCCCCAGGCTCCATCGGCCACCCCGGTGCCCGAGGGC
CCCCTGGATACCGCGGCCCCACCGGAGAGCTGGGGGACCCGGGGCCCAGAGGGGCCCCCGGG
GACCGAGGAGACAAAGGCTCCGCAGGCGCGGGTCTGGACGGGCCGGCCGGGGACCAGGGCCT
CCAAGGACCACAAGGCGTGCCTGGCGTTAGCAAAGACGGCCGCGACGGGCCAACGGCGAGC
CCGGGCCTCCAGGCGATCCTGGCCTCCCCGGTGCTGTGGGTGCTCAGGGGACACCCGGCATC
TGCGACACCTCGGCCTGCCAAGGAGCTGTGATGGGAGGCGGCGGGGAAAAGTCAGGTTCTAG
AAGCTTCTAA
```

Figure 4C. *(SEQ ID NO:6)* gctgccactgggctcctttcttcgccggcgcggcgcggggcggggggcgggcggaagccccaggtgggcccggctgaatggggg
gcttgtgcgcgcrgggcgggacctggccgggggcccgcgccrcccgccgccccgccygtccgcccgagccccggcgcccag
ccccgccgcccagaggcgcgcagagccgctgagagcgcgggcgcagccatggccggggccccacgctggccctgctcctgct

Figure 4D. *(SEQ ID NO:7)* gctgccactgggctcctttcttcgccggcgcggcgcggggcggggggcgggcggaagccccaggtgggcccggctgaatggggg
gcttgtgcgcgcagggcgggacctggccgggggcccgcgccgcccgccgccccgcccgtccgcccgagccccggcgcccag
ccccgccgcccagaggcgcgcagagccgctgagagcgcgggcgcagccatggccggggGccccacgctggccctgctcctg
ct

SEQUENCE LISTING

```
<160> NUMBER OF SEQ ID NOS: 61

<210> SEQ ID NO 1
<211> LENGTH: 2339
<212> TYPE: DNA
<213> ORGANISM: Canis familiaris

<400> SEQUENCE: 1
cctgtcagct tacttcctat aaactccaaa ttcctcctcg gtccattagg cagagcaatc     60
aaattctccc aaattcagct ccaggaacac ctctcaaagc ccagggccct ttgctcacaa    120
tgccacgcgg ggttggactt tcccaggctc cagaggggtt tctcctggac tattttagct    180
gaccttgtgg attttctccc ccatgctggg cacaggactg gtaaacaaag tatattctcc    240
ataaatcata atgaaagctg aaatttatga agccctact acttcatatg aagtacttag    300
catcatctca ttcaatcttc acaaaaattc tataagatag gattattatt atcccctttt    360
acagaggagg acactatatg gtttcaggtg cctgtggtca ccgttagcga cagattccaa    420
```

```
agcacttcac caacattgct taagggaagg aaaagggagc taagagactg ggagaggggt      480
gatgctggac aaacggggga gggggagtgc ttcatggagg aggtcacccc gagggatacc      540
tagagactct ggtgcttcaa gaagctgcag tgaagaaaag gcaaggtgag gagaaggggg      600
aggaggagga ggaggaagag gaggaggtgg aggaggagga ggaggacgct ggacggtggg      660
ggcctgggca gggaggcttc aaggagagca tggccaaggg cggctccagg agcaacagga      720
gcttcagtgc ttccgggggc actaagaggg cctggggctc gctggtggcc tccaaaagcc      780
tgacctccta gctgcggcgg gagcaggag gtgagaggga gatgaggggg tctggaggtg       840
cggcacgggg tgcatggggg ggctcccggg accgccgacc cgtaaggctt gtggtaggct      900
ttcctgcaga agaggcctgc cggtctgtgc tgctaagcca ggtgggtggg ggcctctgcg      960
aactggggtg caggacccgg gcggtggggg cctctgcgac ctgggtgca ggacccacgg      1020 ctcgctctcg gcctgcgccc tggagcagag gagcgacggg ccgaggctcg gcccggggtc      1080
aggctgcagg ggcccccccg acggccgcg cctcccctcg ggggcagagg gtgggcgctg      1140
gctgcggcgc cgggcggggc ggagctgcgc gggcctcggc ccctcggccg ccctctcggg      1200
tgacggcccc gcgccccccg ccccgccccg ccgcatattc aggcgcccgc ccgcccgccc      1260
cgtccgagag cagcccgcgc cgcccgcccg cccgagcctc cgccgcccgc atggccgccg      1320
cccgccgcct cctgctgctg ctccaggggc tcgcgctcgc cctggcgcag atcgtaagtg      1380
ccgcggccgc cgcgcggggt cggggtgcgg ggggcggggg cggggacggg tcgggtgcg      1440 ggcctcggcg cttcccctcg gcggggcgca cagcgggcgc gtccgggcgc gcgcgaggag      1500 gcggagggggc ccggggagcc aggggggccc tgtccggagg cgcgcggccc ggcctgggac      1560
aggcggcgcg gccgggagcc ccgagagccc gggtggcggg cgagacaatg gtgcccattc      1620
acggggctcc ggtgcccsgg cgccgcctcc ccccggggg ctccagccag acgccgctcg      1680
gccccgctgc cgggggccac cggggcgcgg ggacccaccg ggaccggccc gggcgccaag      1740
cctggcacct cgctgcgcgg agggcgcggg cccggggcgg ggggggggc tgccccgcgg      1800 agggcaagcc aacgggaaac ggaggggctc cgggagggg cgcccccgc gtgctccttt      1860 cgggttaggc gcgccaggcg cagggggcag ggcacccgct caccgtcggt acctgtcgtg      1920
cgagcgagcg gtcccggagc ccgccgtcgc ctgcccgctg ggaccgcgg cgccccrgtc      1980 tcccgctccg tccaccgccc tccgccctcc gccctccgcc ctccgcgacc gcgcacgggc      2040 cccgcggggcc agcgcaccgg gacgcgctcc gcgctcgctc tccggagcc gggtcccccc      2100 gcggccaacc cggggccgcg cctcgggtcc tgagcgccgg gaggggcacc cagggcgccg      2160
cacagtcggt tccccgtgag cgcgccgcgc ccggggggg ctctccgcag gaccccgc        2220 cccctgcacc gtctgagggc ctccccctgt gtgtgttctc agagaggtcc gcccggagaa     2280
ccggggcccc cgggcccccc ggggccgccg ggagtgcctg gatccgacgg catcgacgt      2339
```

<210> SEQ ID NO 2
<211> LENGTH: 1644
<212> TYPE: DNA
<213> ORGANISM: Canis familiaris

<400> SEQUENCE: 2

```
catctctccc tcactccctc ctcctgtcag cttacttcct ataaactcca aattcctcct       60
cggtccatta ggcagagcaa tcaaattctc ccaaattcag ctccaggaac acctctcaaa      120
gcccagggca ctttgctcac aatgccacgc ggggttggac tttcccaggc tccagagggg      180
tttctcctgg actattttag ctgaccttgt ggattttctc ccccatgctg ggcacaggac      240
```

```
tggtaaacaa agtatattct ccataaatca taatgaaagc tgaaatttat gaagcccta      300 ctacttcata tgaagtactt agcatcatct cattcaatct tcacaaaaat tctataagat      360
aggattatta ttatcccctt ttacagagga ggacactata tggtttcagg tgcctgtggt      420
caccgttagc gacagattcc aaagcacttc accaacattg cttaagggaa ggaaaaggga      480
gctaagagac tggagagggg tgatgctgg acaaacgggg gaggggagt gcttcatgga       540 ggaggtcacc ccgagggata cctagagact ctggtgcttc aagaagctgc agtgaagaaa      600
aggcaaggtg aggagaaggg ggaggaggag gaggaggaag aggaggaggt ggaggaggag      660
gaggaggacg ctggacggtg ggggcctggg cagggaggct tcaaggagag catggccaag      720
ggcggctcca ggagcaacag gagcttcagt gcttccgggg gcactaagag ggcctggggc      780
tcgctggtgg cctccaaaag cctgacctcc tagctgcggc gggagcaggg aggtgagagg      840
gagatgaggg ggtctggagg tgcggcacgg ggtgcatggg ggggctcccg ggaccgccga      900
cccgtaaggc ttgtggtagg ctttcctgca aagaggcct gccggtctgt gctgctaagc       960
caggtgggtg ggggcctctg cgaactgggg tgcaggaccc gggcggtggg ggcctctgcg     1020 acctggggtca caggacccac ggctcgctct cggcctgcgc cctggagcag aggagcgacg    1080
ggccgaggct cggcccgggg tcaggctgca ggggccccc cgacggccgg cgcctcccct     1140 cggggggcaga gggtgggcgc tggctgcggg gccgggcggg gcggagctgc gcgggcctcg    1200
gcccctcggc cgccctctcg ggtgacggcc ccgcggcccc cgccccgccc cgccgcatat    1260
tcaggcgccc gcccgcccgc cccgtccgag agcagcccgc gccgcccgcc cgcccgagcc    1320
tccgccgccc gcatggccgc cgcccgccgc ctcctgctgc tgctccaggg gctcgcgctc    1380
gccctggcgc agatcgtaag tgccgcgcc gcgcgcggg gtcggggtgc ggggcggg        1440 ggcggggacg ggtcggggtg cgggcctcgg cgcttcccct cggcggggcg cacagcgggc    1500
gcgtccgggc gccgcgaggg aggcggaggg gccgggggag ccaggggggc cctgtccgga    1560
ggcgcgcggc ccggcctggg acaggcggcg cggccgggag ccccgagagc ccgggtggcg    1620
ggcgagacaa tggtgcccat tcac                                             1644
```

<210> SEQ ID NO 3
<211> LENGTH: 2180
<212> TYPE: DNA
<213> ORGANISM: Canis familiaris

<400> SEQUENCE: 3

```
ccgcgccgcc cgcccgcccg agcctccgcc gcccgcatgg ccgccgcccg ccgcctcctg       60
ctgctgctcc aggggctcgc gctcgccctg gcgcagatca gaggtccgcc cggagaaccg     120
gggcccccgg gcccccggg gccgccggga gtgcctggat ccgacggcat cgacggtgac     180 aaggggycc ctgggaaagc cggccctccg ggactgaagg gagagcctgg caaacccggg     240
ccagatgggc ctgatgggaa gcctgggatt gatggtctaa ctggagccaa ggggagcct      300 ggccccatgg ggatccctgg agtcaagggc cagcctgggc tccccggtcc ccctggcctg     360 ccgggcccctg gctttgctgg acctcctgga ccacctggac ctgttggcct cccggtgag    420 attggaatca caggccccaa gggggatccc ggaccagatg ggccatcggg gccccgggg      480 ccacctggca aaccgggccg accggaacc atcagggcc tggaaggcag cgcggatttc      540
ttgtgtccga ccaactgtcc ggcaggggtg aaaggccccc cagggctgca gggggtgaag     600
gggcatcctg gcaaacgcgg ggttctggc gattctggcc gccaggggaa gcgggtccc      660 aagggagatg tgggtgcctc tggagagcaa ggcatccctg gaccaccggg tccccagggc    720
```

```
atcagggct acccgggcat ggagggaccc aaaggagaga tgggtcctcg tgggtacaaa      780
ggcatggtgg gctccattgg tgctgccggg tcacccggtg aggaaggtcc acggggccca    840
ccgggccgag cggggagaa gggcgatgtg ggtggccaag gtctccgagg acctcagggc     900
ataacaggcc cgaagggagc aaccgggccc ccaggcatcg atggcaagga tgggacccca    960
ggcacgccag gcatgaaggg cagtgcggga caggcagggc ggccaggaaa ccaaggccac    1020
caaggcctag cgggcgtgcc gggccagcct gggacaaaag gaggcccggg agacaagggt   1080
gaaccaggcc agcagggcct ccctggattc tctggtcccc ctgggaagga gggagagcca    1140
ggacctcaag gagaaatcgg accccgaggc atcatggggc agaagggtga ccagggtgag    1200 aggggccgg tggggcagcc aggccctcag gacggcagg gccccaaggg ggagcagggc      1260
ccccccggaa ttccagggcc caaggcttg ccaggcatca agggagacaa gggcttcccg     1320
gggaagaccg gccccgcgg cagcgtgggc gacccggggg tggccggcct ccggggagag    1380
aaaggcgaga agggcgagtc cggcgagccg gggcccaagg acagcaagg agtccgcgga    1440 gaagccggct acccgggccc cagcggggat gcgggcgccc cggggtgca gggctacccc    1500 gggccccccg ccctcgagg actgcggga gaccgaggcg tgcccggact gcccgggaga     1560
cagggcgtgg cgggccggga cgccagcgac cagcacatcg tgaccgtgat gatgaagatg    1620
atgcaagagc aactggcaga ggtcgctgtg agtgccaagc ggggaggccct gggtgccatc    1680 gggatggtgg gtccgccagg accccccggg cctcctgggt acccaggcaa gcagggacct    1740
catgggcacc ctggccctcg gggcgttcct ggcatcgtgg gagccgtggg tcagattggc    1800
aacaccggcc ccaagggaaa acgtggagag aagggtgacc ggggagagat gggacgcggg    1860
caccccggga tgcctgggcc cccgggatc ccagggctcc ccggccggcc cgggcaggca    1920
atcaacggca aggacggggc ccgcggcgcc ccaggggccc cgggggaagc aggccgaccg   1980
ggtccgccgg gccccgcggg gctgcccggc ttctgtgagc ccgcgcctg cctggcagcc    2040 tcggcctacg cctctgcgcg cctcacagag cccggatcca tcaaagggcc atgagcagga    2100
ggccaggaca gagcctggcg ggcatcctgg ggggtggggg gggactagat tccagcgggg    2160
tggacacgca ccccatccct                                                2180

<210> SEQ ID NO 4
<211> LENGTH: 2056
<212> TYPE: DNA
<213> ORGANISM: Canis familiaris

<400> SEQUENCE: 4
atggccgggg ccccccacgc tggccctgct cctgctcgcg cggctcctgg ccgccaccct    60
gaccgggacc ggggcgcaga aagtgggacc tcaaggcccc ccggtcccc aagggccacc     120 tgggaagccg gcaaggatg gcattgatgg agaagctggg cctcccggtc tgcccgggtc    180
cccgggacca acaggggccc cagggaagcc agggaagcca ggagaggccg ggctgccggg    240
actgcccggt gtggacggcc tgacgggca ggacggacct cccggaccca agggcgcacc    300
tggggaacgg ggaagcctgg gaccccgggg gcctccggg ttgggggggca aaggcctccc    360 cggaccccc ggagaggcag gagagagtgg tgtccccggt ggaatcggcc tccgggccc     420 cccgggaccc tctggactgc caggcctccc cggcccccc ggacctcccg acccccgg       480 tcacccaggg gtcctccctg agggcgccac tgaccttcag tgcccggcca tctgcccacc    540
aggccccccc ggtcccccag gaatgccggg gttcaagggg cccaccggct acaaaggaga    600
tcaaggagag gtcggcaagg acggcgagaa gggcgatcct ggcccccctg ggcccgctgg    660
```

```
cgtccctggc tctgtggggc tgcaggggcc tcggggactc cgaggtctgc ccgggccggc    720
tgggccccca ggggatcggg gtcccatcgg attccgaggg ccgccaggga tcccaggagc    780
ccccgggaaa gtgggtgaca gaggcgagag gggcccagag ggtttccgcg ccccaaggg     840 tgaccttggc agacccggcc tcaagggagt ccccgggatg ccgggccgg gcggggagcc    900 gggaatgcca ggcaaggacg gccgggatgg cgtgccggga ctggacggcg agaagggaga    960
ggccggtcgc aacggtgccc caggagagaa gggtcccaac gggctgccgg gcctcccggg    1020
tcgagcaggg tccaagggcg agaagggaga actgggccga gctggagagc tgggggaggc    1080
tggcccctcg ggagagcctg gcatcccggg ggacgttggc gtgcctgggg agcgtggtga    1140
ggctggccac aggggctcgg cggggctct gggcccacaa ggccctcctg gagcccctgg    1200
cgtccgcggc ttccagggcc agaagggcag catgggcgac cccggcctgc cggtccccca    1260
gggcctccga ggtgcctcag gtgaccgggg cccgggggga ccgcaggcc ctaagggaga    1320 ccagggcgtt gcaggttccg acggcctccc tgggacaaa ggagagctgg gtcccggtgg    1380
cccggtcgga cccaaaggag aggctggcag tcgagggag ctgggcccca agggcatcca    1440
gggtcccaat ggcaccagcg gcgtcgaggg cctcccgggc ccgcccggcc ccgtgggctt    1500
cccgggcgtc cagggcgtgc ccggcatcac cgggaaaccg ggggttccgg ggcgagaagc    1560
cagcgagcag cacatccggg agctgtgcgg ggggatgctc agcgaacaaa tcgcgcagtt    1620
ggccgctcac ctgaggaagc ctctggcgcc cggatccgcc gggcggcctg ggccagcggg    1680
gcccccaggc ccccgggge cccaggctc catcggccac cccggtgccc gagggccccc    1740
tggataccgc ggccccaccg gagagctggg ggacccgggg cccagagggg ccccgggga    1800 ccgaggagac aaaggctccg caggcgcggg tctggacggg ccggccgggg accagggcct    1860
ccaaggacca caaggcgtgc ctggcgttag caaagacggc cgcgacgggg ccaacggcga    1920
gcccgggcct ccaggcgatc ctggcctccc cggtgctgtg ggtgctcagg gacacccgg    1980 catctgcgac acctcggcct gccaaggagc tgtgatggga ggcggcgggg aaaagtcagg    2040
ttctagaagc ttctaa                                                   2056
```

<210> SEQ ID NO 5
<211> LENGTH: 2055
<212> TYPE: DNA
<213> ORGANISM: Canis familiaris

<400> SEQUENCE: 5

```
atggccgggg cccccacgct ggccctgctc ctgctcgcgc ggctcctggc cgccaccctg     60
accgggaccg gggcgcagaa agtgggacct caaggccccc ccgtccccca gggccacct    120 gggaagccgg gcaaggatgg cattgatgga gaagctgggc ctcccggtct gcccgggtcc    180
ccgggaccaa caggggcccc agggaagcca gggaagccag gagaggcgg gctgccrgga    240 ctgcccggtg tggacggcct gacggggcag gacggacctc ccggacccaa gggcgcacct    300
ggggaacrgg gaagcctggg accccegggg cctcccgggt tggggggcaa aggcctcccc    360
ggaccccccg gagaggcagg agagagtggt gtccccggtg gaatcggcct ccggggcccc    420
ccgggaccct ctggactgcc aggcctcccc ggccccccg gacctccgg acccccggt     480 cacccagggg tcctccctga gggcgccact gaccttcagt gccggccat tgcccacca     540 ggcccccccg gtccccagg aatgccgggg ttcaggggc caccggcta caaggagat     600 caaggagagg tcgcaagga cggcgagaag ggcgatcctg gccccctgg gcccgctggc    660 gtccctggct ctgtggggct gcaggggcct cgggactcc gaggtctgcc cgggccggct    720
```

```
gggcccccag gggatcgggg tcccatcgga ttccgagggc cgccagggat cccaggagcc      780
cccgggaaag tgggtgacag aggcgagagg ggcccagagg gtttccgcgg ccccaagggt      840
gaccttggca gacccggcct caagggagtc cccgggatgg ccgggccggg cggggagccg      900
ggaatgccag gcaaggacgg ccgggatggc gtgccgggac tggacggcga aagggagag       960 gccggtcgca acggtgcccc aggagagaag ggtcccaacg ggctgccggg cctcccgggt     1020
cgagcagggt ccaagggcga aagggagaa ctgggccgag ctggagagct gggggaggct     1080
ggcccctcgg gagagcctgg catcccgggg gacgttggcg tgcctgggga gcgtggtgag     1140
gctggccaca ggggctcggc gggggctctg gcccacaag gccctcctgg agccctggc       1200 gtccgcggct tccagggcca gaagggcagc atgggcgacc ccggcctgcc gggtccccag     1260
ggcctccgag gtgcctcagg tgaccgggc ccgggggag ccgcaggccc taagggagac      1320
cagggcgttg caggttccga cggcctccct ggggacaaag gagagctggg tcccggtggc     1380
ccggtcggac ccaaaggaga ggctggcagt cgaggggagc tgggccccaa gggcatccag     1440
ggtcccaayg gcaccagcgg cgtcgagggc ctcccgggcc cgcccggccc cgtgggcttc     1500
ccgggcgtcc agggcgtgcc cggcatcacc gggaaaccgg gggttccggg gcgagaagcc     1560
agcgagcagc acatccggga gctgtgcggg gggatgctca gcgaacaaat cgcgcagttg     1620
gccgctcacc tgaggaagcc tctggcgccc ggatccgccg gcggcctgg gccagcgggg      1680 cccccaggcc cccgggggcc cccaggctcc atcggccacc ccgtgcccg agggccccct      1740 ggataccgcg gccccaccgg agagctgggg gacccggggc ccagaggggc ccccggggac     1800
cgaggagaca aaggctccgc rggcgcgggt ctggacgggc cggccgggga ccagggcctc     1860
caaggaccac aaggcgtgcc tggcgttagc aaagacggcc gcgacgggc caacggcgag     1920 cccgggcctc caggcgatcc tggcctcccc ggtgctgtgg gtgctcaggg gacacccggc     1980
atctgcgaca cctcggcctg ccaaggagct gtgatgggag gcggcgggga aaagtcaggt     2040
tctagaagct tctaa                                                     2055

<210> SEQ ID NO 6
<211> LENGTH: 248
<212> TYPE: DNA
<213> ORGANISM: Canis familiaris

<400> SEQUENCE: 6
gctgccactg ggctcctttc ttcgccggcg cggcgcgggg cggggcggg cggaagcccc        60 aggtgggccc ggctgaatgg ggggcttgtg cgcgcrgggc gggacctggc cggggcccg       120 cgccrcccgc cgccccgccy gtccgcccga gccccggcgc cccagccccg ccgcccagag      180
gcgcgcagag ccgctgagag cgcgggcgca gccatggccg gggcccccac gctggccctg      240
ctcctgct                                                               248

<210> SEQ ID NO 7
<211> LENGTH: 249
<212> TYPE: DNA
<213> ORGANISM: Canis familiaris

<400> SEQUENCE: 7
gctgccactg ggctcctttc ttcgccggcg cggcgcgggg cggggcggg cggaagcccc        60 aggtgggccc ggctgaatgg ggggcttgtg cgcgcagggc gggacctggc cggggcccg       120 cgccgcccgc cgccccgccc gtccgcccga gccccggcgc cccagccccg ccgcccagag      180
gcgcgcagag ccgctgagag cgcgggcgca gccatggccg gggcccccca cgctggccct      240
``` gctcctgct                                                                    249

<210> SEQ ID NO 8
<211> LENGTH: 20
<212> TYPE: DNA
<213> ORGANISM: Canis familiaris

<400> SEQUENCE: 8
ccgccccgtc cgagagcagc                                                         20

<210> SEQ ID NO 9
<211> LENGTH: 22
<212> TYPE: DNA
<213> ORGANISM: Canis familiaris

<400> SEQUENCE: 9
gcttcccatc aggcccatct gg                                                      22

<210> SEQ ID NO 10
<211> LENGTH: 20
<212> TYPE: DNA
<213> ORGANISM: Canis familiaris

<400> SEQUENCE: 10
gagcctccgc cgcccgcatg                                                         20

<210> SEQ ID NO 11
<211> LENGTH: 22
<212> TYPE: DNA
<213> ORGANISM: Canis familiaris

<400> SEQUENCE: 11
gctccagtta gaccatcaat cc                                                      22

<210> SEQ ID NO 12
<211> LENGTH: 18
<212> TYPE: DNA
<213> ORGANISM: Canis familiaris

<400> SEQUENCE: 12
ctggcgcaga tcagaggt                                                           18

<210> SEQ ID NO 13
<211> LENGTH: 20
<212> TYPE: DNA
<213> ORGANISM: Canis familiaris

<400> SEQUENCE: 13
cagttggtcg gacacaagaa                                                         20

<210> SEQ ID NO 14
<211> LENGTH: 21
<212> TYPE: DNA
<213> ORGANISM: Canis familiaris

<400> SEQUENCE: 14
cctggatccg acggcatcga c                                                       21

<210> SEQ ID NO 15
<211> LENGTH: 22
<212> TYPE: DNA
<213> ORGANISM: Canis familiaris

<400> SEQUENCE: 15

```
gtggtccagg aggtccagca aa                                              22

<210> SEQ ID NO 16
<211> LENGTH: 21
<212> TYPE: DNA
<213> ORGANISM: Canis familiaris

<400> SEQUENCE: 16
tgggattgat ggtctaactg g                                               21

<210> SEQ ID NO 17
<211> LENGTH: 20
<212> TYPE: DNA
<213> ORGANISM: Canis familiaris

<400> SEQUENCE: 17
gggtccgatt tctccttgag                                                 20

<210> SEQ ID NO 18
<211> LENGTH: 20
<212> TYPE: DNA
<213> ORGANISM: Canis familiaris

<400> SEQUENCE: 18
ctccctggat tctctggtcc                                                 20

<210> SEQ ID NO 19
<211> LENGTH: 20
<212> TYPE: DNA
<213> ORGANISM: Canis familiaris

<400> SEQUENCE: 19
gcccttctcg cctttctctc                                                 20

<210> SEQ ID NO 20
<211> LENGTH: 22
<212> TYPE: DNA
<213> ORGANISM: Canis familiaris

<400> SEQUENCE: 20
cttgccaggc atcaagggag ac                                              22

<210> SEQ ID NO 21
<211> LENGTH: 23
<212> TYPE: DNA
<213> ORGANISM: Canis familiaris

<400> SEQUENCE: 21 ggtcacccttt ctctccacgt ttt                                            23

<210> SEQ ID NO 22
<211> LENGTH: 22
<212> TYPE: DNA
<213> ORGANISM: Canis familiaris

<400> SEQUENCE: 22
atcaagggag acaagggctt cc                                              22

<210> SEQ ID NO 23
<211> LENGTH: 21
<212> TYPE: DNA
<213> ORGANISM: Canis familiaris

<400> SEQUENCE: 23
```
ctcacagcga cctctgccag t                               21

<210> SEQ ID NO 24
<211> LENGTH: 21
<212> TYPE: DNA
<213> ORGANISM: Canis familiaris

<400> SEQUENCE: 24
cgaccagcac atcgtgaccg t                               21

<210> SEQ ID NO 25
<211> LENGTH: 20
<212> TYPE: DNA
<213> ORGANISM: Canis familiaris

<400> SEQUENCE: 25
tccttgccgt tgattgcctg                                 20

<210> SEQ ID NO 26
<211> LENGTH: 23
<212> TYPE: DNA
<213> ORGANISM: Canis familiaris

<400> SEQUENCE: 26
ccaagggaaa acgtggagag aag                             23

<210> SEQ ID NO 27
<211> LENGTH: 23
<212> TYPE: DNA
<213> ORGANISM: Canis familiaris

<400> SEQUENCE: 27
gaaagctggc ttcctggtct gag                             23

<210> SEQ ID NO 28
<211> LENGTH: 20
<212> TYPE: DNA
<213> ORGANISM: Canis familiaris

<400> SEQUENCE: 28
gcgcgcagag ccgctgagag                                 20

<210> SEQ ID NO 29
<211> LENGTH: 20
<212> TYPE: DNA
<213> ORGANISM: Canis familiaris

<400> SEQUENCE: 29
attccaccgg ggacaccact                                 20

<210> SEQ ID NO 30
<211> LENGTH: 18
<212> TYPE: DNA
<213> ORGANISM: Canis familiaris

<400> SEQUENCE: 30
ggaggacccc tgggtgac                                   18

<210> SEQ ID NO 31
<211> LENGTH: 21
<212> TYPE: DNA
<213> ORGANISM: Canis familiaris

<400> SEQUENCE: 31

-continued cgacctctcc ttgatctcct t                                              21

<210> SEQ ID NO 32
<211> LENGTH: 20
<212> TYPE: DNA
<213> ORGANISM: Canis familiaris

<400> SEQUENCE: 32
gcagaaagtg ggacctcaag                                                20

<210> SEQ ID NO 33
<211> LENGTH: 20
<212> TYPE: DNA
<213> ORGANISM: Canis familiaris

<400> SEQUENCE: 33
aagccaggga agccaggaga                                                20

<210> SEQ ID NO 34
<211> LENGTH: 21
<212> TYPE: DNA
<213> ORGANISM: Canis familiaris

<400> SEQUENCE: 34
agaggcagga gagagtggtg t                                              21

<210> SEQ ID NO 35
<211> LENGTH: 20
<212> TYPE: DNA
<213> ORGANISM: Canis familiaris

<400> SEQUENCE: 35
cttgccgacc tctccttgat                                                20

<210> SEQ ID NO 36
<211> LENGTH: 20
<212> TYPE: DNA
<213> ORGANISM: Canis familiaris

<400> SEQUENCE: 36
aacgccctgg tctcccttag                                                20

<210> SEQ ID NO 37
<211> LENGTH: 21
<212> TYPE: DNA
<213> ORGANISM: Canis familiaris

<400> SEQUENCE: 37
gaagggagaa ctgctggaga g                                              21

<210> SEQ ID NO 38
<211> LENGTH: 20
<212> TYPE: DNA
<213> ORGANISM: Canis familiaris

<400> SEQUENCE: 38
gatttgttcg ctgagcatcc                                                20

<210> SEQ ID NO 39
<211> LENGTH: 20
<212> TYPE: DNA
<213> ORGANISM: Canis familiaris

<400> SEQUENCE: 39

-continued ctggggacaa aggagagctg    20

<210> SEQ ID NO 40
<211> LENGTH: 21
<212> TYPE: DNA
<213> ORGANISM: Canis familiaris

<400> SEQUENCE: 40
cccgaggtac gatgttagag c    21

<210> SEQ ID NO 41
<211> LENGTH: 21
<212> TYPE: DNA
<213> ORGANISM: Canis familiaris

<400> SEQUENCE: 41
tgtggtaggc tttcctgaag a    21

<210> SEQ ID NO 42
<211> LENGTH: 20
<212> TYPE: DNA
<213> ORGANISM: Canis familiaris

<400> SEQUENCE: 42
cccgacccag gttagagact    20

<210> SEQ ID NO 43
<211> LENGTH: 21
<212> TYPE: DNA
<213> ORGANISM: Canis familiaris

<400> SEQUENCE: 43
aaaagcctga cctcctagct g    21

<210> SEQ ID NO 44
<211> LENGTH: 23
<212> TYPE: DNA
<213> ORGANISM: Canis familiaris

<400> SEQUENCE: 44
ccggttctgt gctgctaagc cag    23

<210> SEQ ID NO 45
<211> LENGTH: 21
<212> TYPE: DNA
<213> ORGANISM: Canis familiaris

<400> SEQUENCE: 45
gagcctccgc cgccccgcat g    21

<210> SEQ ID NO 46
<211> LENGTH: 21
<212> TYPE: DNA
<213> ORGANISM: Canis familiaris

<400> SEQUENCE: 46
cgcctaaccc gaaaggagca c    21

<210> SEQ ID NO 47
<211> LENGTH: 21
<212> TYPE: DNA
<213> ORGANISM: Canis familiaris

<400> SEQUENCE: 47
ctgctgctgc tccaggggct c          21

<210> SEQ ID NO 48
<211> LENGTH: 21
<212> TYPE: DNA
<213> ORGANISM: Canis familiaris

<400> SEQUENCE: 48
gcccggttct gtgctgctaa g          21

<210> SEQ ID NO 49
<211> LENGTH: 20
<212> TYPE: DNA
<213> ORGANISM: Canis familiaris

<400> SEQUENCE: 49
gtgaatgggc accattgtct            20

<210> SEQ ID NO 50
<211> LENGTH: 19
<212> TYPE: DNA
<213> ORGANISM: Canis familiaris

<400> SEQUENCE: 50
ccggttctgt gctgctaag             19

<210> SEQ ID NO 51
<211> LENGTH: 19
<212> TYPE: DNA
<213> ORGANISM: Canis familiaris

<400> SEQUENCE: 51
cctaacccga aaggagcac             19

<210> SEQ ID NO 52
<211> LENGTH: 22
<212> TYPE: DNA
<213> ORGANISM: Canis familiaris

<400> SEQUENCE: 52
gctgaccttg tggattttct cc         22

<210> SEQ ID NO 53
<211> LENGTH: 20
<212> TYPE: DNA
<213> ORGANISM: Canis familiaris

<400> SEQUENCE: 53
gtgaatgggc accattgtct            20

<210> SEQ ID NO 54
<211> LENGTH: 22
<212> TYPE: DNA
<213> ORGANISM: Canis familiaris

<400> SEQUENCE: 54
catctctccc tcactccctc ct         22

<210> SEQ ID NO 55
<211> LENGTH: 23
<212> TYPE: DNA
<213> ORGANISM: Canis familiaris

<400> SEQUENCE: 55

```
tcacccctct cccagtctct tag                                              23

<210> SEQ ID NO 56
<211> LENGTH: 24
<212> TYPE: DNA
<213> ORGANISM: Canis familiaris

<400> SEQUENCE: 56
gctgccactg ggctcctttc ttcg                                             24

<210> SEQ ID NO 57
<211> LENGTH: 21
<212> TYPE: DNA
<213> ORGANISM: Canis familiaris

<400> SEQUENCE: 57
agcaggagca gggccagcgt g                                                21

<210> SEQ ID NO 58
<211> LENGTH: 20
<212> TYPE: DNA
<213> ORGANISM: Canis familiaris

<400> SEQUENCE: 58
cgctcacatg cgccccggtc                                                  20

<210> SEQ ID NO 59
<211> LENGTH: 20
<212> TYPE: DNA
<213> ORGANISM: Canis familiaris

<400> SEQUENCE: 59
ggcgcagcca tggccgggac                                                  20

<210> SEQ ID NO 60
<211> LENGTH: 22
<212> TYPE: DNA
<213> ORGANISM: Canis familiaris

<400> SEQUENCE: 60
ggtcagggtg gcggccagga gc                                               22

<210> SEQ ID NO 61
<211> LENGTH: 20
<212> TYPE: DNA
<213> ORGANISM: Canis familiaris

<400> SEQUENCE: 61
ggcgcagcca tggccgggcg                                                  20
```

METHOD FOR IDENTIFYING OCULOSKELETAL DYSPLASIA IN DOGS

This application claims priority to U.S. patent application Ser. No. 60/968,150, filed on Aug. 27, 2007, the disclosure of which is incorporated herein by reference.

This invention was supported by government funding under grant no. EY06855 from the National Institutes of Health. The Government has certain rights in the invention.

FIELD OF THE INVENTION

The present invention relates generally to a canine disease termed Oculo-skeletal dysplasia. More particularly, the invention relates to compositions and methods for use in testing dogs for Oculo-skeletal dysplasia.

DESCRIPTION OF RELATED ART

Oculo-skeletal dysplasia (OSD) is an autosomal recessive disorder that has been observed in 2 dog breeds, Labrador retriever (Carrig et al. JAVMA (1977) 170:49-57) and Samoyed (Meyers et al., JAVMA (1983) 183:975-979), but mutations associated with the disease may be present in other breeds.

Dogs that are affected with OSD have skeletal abnormalities characterized by short-limbed dwarfism and ocular defects including vitreous dysplasia, retinal detachment and cataracts. Dogs affected with OSD can usually be recognized upon physical examination by an experienced veterinarian, particularly an experienced veterinary ophthalmologist, or an experienced veterinary orthopedist, and sometimes by experienced dog breeders. However, recognition of affected dogs is not sufficient to allow adequate selection pressure to be applied to significantly reduce the frequency of a mutation that may be associated with OSD in the population. Furthermore, while it is widely held that OSD carriers can usually be recognized upon physical examination by an experienced veterinary ophthalmologist via detecting retinal folds or retinal dysplasia, this is highly unreliable as both false positive and false negative diagnoses are common. Thus, ophthalmoscopic examination to detect carriers is too inaccurate to allow adequate selection pressure to be applied to significantly reduce frequency of mutation(s) in the population that may be associated with OSD. Thus, improved methods for determining the likelihood of a dog to be a carrier, affected with, or normal for OSD are needed.

SUMMARY OF THE INVENTION

The present invention is based on our discovery of mutations associated with oculo-skeletal dysplasia (OSD). The OSD mutations analyzed in the method of the invention are referred to as the drd1 COL9A3 mutation and the drd2 COL9A2 mutation. These mutations are also referred to herein as the drd1 mutation and the drd2 mutation, respectively. drd1 and drd2 refer to dwarfism-retinal-dysplasia 1 and 2, respectively. The method comprises obtaining a biological sample from a dog and determining from the sample the presence or absence of the drd1 mutation, the presence or absence of the drd2 mutation, or the presence or absence of both of these mutations. Dogs that do not have either of these mutations (homozygous for the wild type sequence) are considered normal for OSD. Dogs that are heterozygous for the drd1 mutation are considered drd1 mutation carriers. drd1 mutation carriers are considered to be carriers of a drd1 form of OSD. Dogs that are heterozygous for the drd2 mutation are considered drd2 mutation carriers. drd2 mutation carriers are considered to be carriers of a drd2 form of OSD. Dogs that are homozygous for either the drd1 mutation or the drd2 mutation are considered to be affected with OSD.

The present invention also provides a method for selective breeding of dogs, whereby dogs that are identified as carriers of either OSD mutation, or as affected with OSD can be removed from the breeding stock. Also provided are kits useful for carrying out the methods of the invention.

BRIEF DESCRIPTION OF THE DRAWINGS

FIG. 1 provides the genomic sequence of the 5' end of the canine COL9A2 gene.

FIG. 2 provides the nucleotide sequence of the region of the COL9A2 gene which encompasses the COL9A2 drd2 mutation.

FIG. 3 provides the canine COL9A2 cDNA sequence.

FIG. 4A provides the wild type canine COL9A3 drd1 cDNA coding sequence.

FIG. 4B provides the mutant canine COL9A3 drd1 cDNA coding sequence.

FIG. 4C provides the provides the genomic sequence of the 5' end of COL9A3 gene in a normal CFA24 chromosome.

FIG. 4D provides the genomic sequence of the 5' end of COL9A3 in a CFA24 chromosome that comprises the drd1 mutation.

DETAILED DESCRIPTION OF THE INVENTION

Figure 5A:
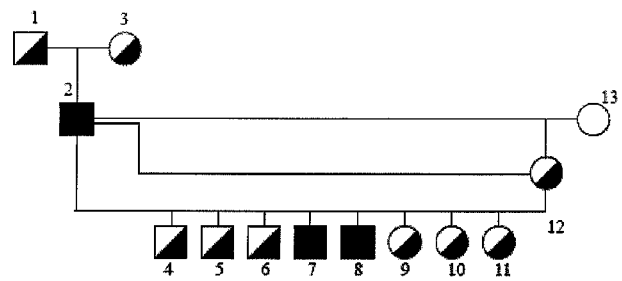
FIG. 5A provides a pedigree of a colony of dogs descended from a purebred Samoyed affected with OSD.

The present invention provides a method for determining whether a dog is normal for OSD, or is a carrier of an OSD mutation, or is affected with OSD. The invention is based on our discovery of genetic mutations associated with OSD. In particular, we have discovered a mutation that is a 1,267 base pair deletion in the canine COL9A2 gene on canine chromosome 15 (CFA15) (the drd2 COL9A2 mutation) and a mutation that is a one nucleotide (a guanine; "G") insertion in the canine COL9A3 gene on canine chromosome 24 (CFA24) (the drd1 COL9A3 mutation).

The term "drd1 COL9A3 mutation" is used interchangeably herein with "drd1 mutation." Likewise, the term "drd2 COL9A2 mutation" is used interchangeably with "drd2 mutation." The drd1 mutation and the drd2 mutation can each be referred to individually as an "OSD mutation" and collectively as "OSD mutations."

As used herein, a dog is termed "normal" or "normal for OSD" if the dog does not have either OSD mutation (i.e., the dog is homozygous wild type for both OSD mutation sites). A dog is termed "affected" or "affected with OSD" if the dog is homozygous for either or both OSD mutations. A dog is a carrier of OSD if it is heterozygous for either the drd1 mutation or the drd2 mutation, or for both mutations. A "drd1 mutation carrier" as used herein means a dog that is heterozygous for the drd1 mutation. A drd1 mutation carrier is considered to be a carrier of drd1 form of OSD. A "drd2 mutation carrier" as used herein means a dog that is heterozygous for the drd2 mutation. A drd2 mutation carrier is considered to be a carrier of drd2 form of OSD. Determining that a dog is a drd1 mutation carrier does not indicate whether or not the dog is a drd2 mutation carrier, or whether or not the dog is affected via homozygosity for the drd2 mutation. Likewise, determining that a dog is a drd2 mutation carrier does not indicate whether or not the dog is a drd1 mutation carrier, or whether or not the dog is affected via homozygosity for the drd1 mutation.

It will be recognized by those skilled in the art that carriers of either OSD mutation that are not affected with OSD may nevertheless exhibit varying OSD traits, such as an ocular phenotype that ranges from localized retinal dysplasia characterized by focal or multifocal retinal folds to large plaques of dysplastic retinal tissue, but have a normal appendicular skeleton. The present invention addresses this and other difficulties in ascertaining the OSD status of dogs by providing a method for determining whether a dog is normal for OSD, or is a carrier of the drd1 mutation, or is a carrier of the drd2 mutation, or is affected with OSD. The method comprises the steps of obtaining a biological sample from a dog and determining from the biological sample the presence or absence of the drd1 mutation, the drd2 mutation, or both of these mutations. A determination that the dog is homozygous for either OSD mutation is indicative that the dog is affected with OSD. A determination that neither OSD mutation is present is indicative that the dog is normal for OSD. A determination that the dog is heterozygous for the drd1 mutation indicates that the dog is a drd1 mutation carrier, a carrier of drd1 form of OSD. A determination that the dog is heterozygous for the drd2 mutation indicates that the dog is a drd2 mutation carrier, and is therefore a carrier of drd2 form of OSD.

Any dog, regardless of breed, could be heterozygous or homozygous for either or both OSD mutations. To date, we have found the drd1 mutation in Labrador retrievers and the drd2 mutation in Samoyeds. Nevertheless, upon identification of heterozygosity for one OSD mutation, it is preferable to determine the status of the other OSD mutation. For example, upon a determination that a dog is a drd1 mutation carrier, it would be preferable to determine the drd2 status of the dog to ascertain whether or not the dog is also a drd2 mutation carrier, or whether the dog is homozygous for the drd2 mutation, and is therefore affected with OSD, in addition to being a drd1 mutation carrier.

In one embodiment, the method further comprises communicating the result of determining whether a dog is normal for OSD, a drd1 mutation carrier or drd2 mutation carrier, or is affected with OSD to an individual. The test result can be communicated to an individual by any method. Non-limiting examples of the individual to whom the test results may be communicated include the dog owner, a canine pedigree accreditization agency, a veterinarian, or a provider of genetic test results.

We have determined that the drd2 COL9A2 mutation is a 1,267 base pair deletion. The deletion and its genomic context is illustrated by the DNA sequences depicted in FIGS. 1-3.

FIG. 1 provides the genomic sequence of the 5' end of the canine COL9A2 gene (SEQ ID NO:1). This sequence is a corrected version of the 5' region of the canine COL9A2 genomic sequence, and extends from a location 1,310 nucleotides (nts) of SEQ ID NO:1 before the start codon (boxed), to the beginning of intron 2. In particular, we have determined that both the 2004 July CanFam1 and 2005 May CanFam2 assemblies (provided to the public through GenBank) have incorrect and incomplete sequences for this interval of CFA15. In particular, we have determined the 2005 assembly is missing exon 1 and surrounding sequence. We determined this using primers designed from sequence shared by both CanFam assemblies to amplify genomic DNA to retrieve the sequence presented as SEQ ID NO:1. In the corrected sequence presented in SEQ ID NO:1, nucleotide 1 corresponds to nucleotide (nt) 5,649,378 of canine chromosome 15 in the CanFam2 2005 assembly, and nt 5,641,234 of canine chromosome 15 in the CanFam1 2004 assembly. The start codon is at positions 1311-1313 (boxed), exon 1 ends at nt 1373 (and thus contains a 63 base coding sequence), intron 1 extends from nt 1374 through 2262 and exon 2 from nts 2263-2337. Capital letters signify coding regions.

FIG. 2 provides a DNA sequence (SEQ ID NO:2) that illustrates the sequence deleted in the drd2 COL9A2 mutation in the genomic CFA15 DNA context. The region of the canine genomic COL9A2 sequence presented in FIG. 2 encompasses the drd2 mutation (the deletion), and extends from the drd2 5' region, through exon 1, and into the start of intron 1. The ATG of codon 1 is boxed; the coding sequence is shown in uppercase. The drd2 mutation is a deletion of the 1,267 nucleotides between nucleotide number 230 and nucleotide number 1,498 in the nucleotide sequence depicted in FIG. 2. Thus, determining a deletion of 1,267 nucleotides between nucleotide number 230 and nucleotide number 1,498 in the nucleotide sequence depicted in FIG. 2 (SEQ ID NO:2) identifies the presence of the drd2 mutation. The drd2 mutation removes the complete exon 1 of the transcript and its 5' untranslated region (UTR), as well as part of intron 1.

The presence or absence of the drd2 mutation can be detected by any appropriate method, including but not limited to by analysis of canine genomic DNA, mRNA, cDNA, or protein.

In one embodiment, the presence or absence of the drd2 mutation can be determined by PCR analysis. Exemplary PCR primer binding sites useful for PCR based amplification across the deletion are underlined in FIG. 2 (primer pair 1) or double underlined (primer pair 2).

FIG. 3 provides the canine COL9A2 cDNA sequence (SEQ ID NO:3). The first methionine (ATG) and the normal stop (TGA) codons are boxed. Non-coding sequence is shown in lowercase, coding sequence in uppercase. A single nucleotide polymorphism (SNP) identified in exon 3 has 2 alleles (C or T) and is shown as a bold enlarged Y (indicating a pyrimidine). In CFA15 chromosomes that comprise the drd2 mutation, the C allele of this SNP is present, but this allele is also observed in normal dogs of various breeds.

Turning to the drd1 mutation, we have determined that the drd1 mutation is a one nucleotide (guanine) insertion in the canine COL9A3 gene on canine chromosome 24 (CFA24). This insertion is illustrated in FIG. 4B (SEQ ID NO:4), which depicts a cDNA sequence comprising the Canine drd1 COL9A3 mutation. FIG. 4A (SEQ ID NO:5) provides the wild type drd1 COL9A3 cDNA sequence. In FIGS. 4A and 4B, the first methionine (ATG) and the normal stop (TAA) codons are boxed. In a chromosome that contains the drd1 mutation, the extra guanine (G) is inserted into the string of 4 Gs shown at nucleotide positions 7-10 of the normal coding sequence (FIG. 4A), resulting in a string of 5 Gs in the mutant (FIG. 4B). In the mutant sequence shown in FIG. 4B, the inserted G is arbitrarily indicated (bolded and enlarged) as the 5th G in the string at nucleotide position 11 of SEQ ID NO:4, although the insertion could be any one of the 5 Gs. Thus, it is considered that determining a G in position 11 of SEQ ID NO:4 as depicted in FIG. 4B identifies the presence of the drd1 mutation. It is also considered that determining a G in position 11 of SEQ ID NO:4 as depicted in FIG. 4B identifies a nucleotide sequence consisting of GGGGG in positions 7-11 in the nucleotide sequence depicted in FIG. 4B. However, it will be recognized that the invention includes any other method of identifying the presence or absence of the drd1 mutation, including but not limited to by analysis of canine genomic DNA, mRNA, cDNA, or protein. In respect of genomic DNA, FIG. 4C provides the genomic sequence of the 5' end of COL9A3 gene in a normal CFA24 chromosome (SEQ ID NO:6). FIG. 4D provides the genomic sequence of the 5' end of COL9A3 in a CFA24 chromosome that comprises the drd1 mutation (SEQ ID NO:7), wherein the fifth G that signifies the presence of the GGGGG sequence that may be used to identify the drd1 mutation is shown in bold and enlarged. The atg start codon is boxed in FIGS. 4C and 4D.

It will be recognized that identifying the presence or absence of the drd1 mutation by analysis of genomic DNA sequence is well within the purview of one skilled in the art and is included in the present invention. It is accordingly considered that identification of the presence or absence of the drd1 mutation by analysis of genomic DNA sequence also identifies a G in position 11 of SEQ ID NO:4.

Representative primers useful for use in one embodiment of the invention for determining the presence or absence of the drd1 mutation from genomic DNA are underlined in FIGS. 4C and 4D (these primers are also shown as primer pair 3 in Table 2). In FIGS. 4C and 4D, SNPs are shown as bold where r=A or G, y=C or T. The first methionine in the COL9A3 gene is boxed.

The insertion of G in the drd1 mutation alters the drd 1 open reading frame by +1 nucleotide, which introduces a stop codon after 48 codons (TGA; shown in bold and enlarged in FIG. 4B). Thus, the G in position 11 of SEQ ID NO:4 is in the +1 open reading frame relative to the ATG start codon presented in nucleotide positions 1-3 of FIG. 4B. The invention therefore also includes identifying the drd1 COL9A3 mutation using any method by which a +1 translational frameshift introduced into the drd1 COL9A3 gene by the drd1 mutation can be detected.

In addition to the inserted G, we have also identified four SNPs that are shown as bolded and enlarged R or Y in the sequence depicted in FIG. 4A for the wild type drd1 COL9A3 cDNA sequence, where the R indicates a purine (alleles are A or G for the first, second and fourth SNPS shown as R) and Y indicates a pyrimidine (alleles are C or T for the third SNP shown as Y). In CFA24 chromosomes that have the drd1 mutation, we have determined the alleles present for the 4 SNPs are: G, G, T, A (in haplotype order). These are shown in bold and enlarged in the sequence depicted in FIG. 4B. However, this haplotype is also observed in normal dogs.

As noted above, the drd1 mutation creates a +1 translational frameshift and a premature stop codon (TGA) relative to the normal coding sequence. This results in a predicted protein that is altered relative to the normal protein. The predicted altered protein is shorter and has a predicted amino acid sequence that is different from that of the predicted normal drd1 protein. Therefore, the presence of the drd1 mutation could be determined by detecting this altered protein. Similarly, the drd2 mutation also results in a sequence encoding a predicted protein that is altered via a predicted different and shorter amino acid sequence relative to the predicted normal protein. Therefore, the presence of the drd2 mutation could also be determined by detecting this predicted altered protein. Detecting either predicted altered protein would be indicative that the dog is not normal. Such altered proteins could be detected using any conventional technique, such as by immunodetection methods, including but not limited to immunohistochemistry, Western blotting, ELISA, and fluorescent in situ hybridization (FISH).

The biological sample tested in the method of the invention can be any biological sample that contains nucleic acids or protein. For example, a sample of blood, hair, spleen, mucosal scrapings, semen, tissue biopsy, saliva or the like can be used. In one embodiment, the biological sample is blood. Suitable collection techniques for obtaining biological samples from dogs are known in the art.

Techniques for isolating and preparing nucleic acids in a form that is suitable for testing for OSD mutations are well known. Nucleic acids for use in testing for OSD mutations may be tested directly using any suitable method, or may be amplified before testing using a variety of techniques that are well known. For example, genomic DNA or mRNA may be amplified through use of PCR or RT-PCR, respectively (Saiki et al. Science 239:487-491 (1988)). Other suitable in vitro amplification methods include the ligase chain reaction (LCR) (Wu and Wallace Genomics 4:560-569 (1989)), strand displacement amplification (SDA) (Walker et al. PNAS USA 89:392-396 (1992)), and the self-sustained sequence replication (3SR) (Fahy et al. PCR Methods Appl. 1:25-33 (1992)).

Detecting the presence or absence of an OSD mutation in nucleic acids can be accomplished by a variety of methods. Such methods include but are not limited polymerase chain reaction (PCR), hybridization with allele-specific oligonucleotide probes (Wallace et al. Nucl Acids Res 6:3543-3557 (1978)), including immobilized oligonucleotides (Saiki et al. PNAS USA 86:6230-6234 (1989)) or oligonucleotide arrays (Maskos and Southern Nucl Acids Res 21:2269-2270 (1993)), allele-specific PCR (Newton et al. Nucl Acids Res 17:2503-25 16 (1989)), mismatch-repair detection (MRD) (Faham and Cox Genome Res 5:474-482 (1995)), denaturing-gradient gel electrophoresis (DGGE) (Fisher and Lerman et al. PNAS USA 80:1579-1583 (1983)), single-strand-conformation-polymorphism detection (Orita et al. Genomics 5:874-879 (1983)), chemical (Cotton et al. PNAS USA 85:4397-4401 (1988)) or enzymatic (Youil et al. PNAS USA 92:87-91 (1995)) cleavage of heteroduplex DNA, methods based on allele specific primer extension (Syvanen et al. Genomics 8:684-692 (1990)), genetic bit analysis (GBA) (Nikiforov et al. Nuci Acids Res 22:4167-4175 (1994)), the oligonucleotide-ligation assay (OLA) (Landegren et al. Science 241:1077 (1988)), the allele-specific ligation chain reaction (LCR) (Barrany PNAS USA 88:189-193 (1991)), dynamic allele-specific hybridization (DASH), microplate array diagonal gel electrophoresis (MADGE), Pyrosequencing™, any of various DNA "chip" technologies, such as those offered by AFFYMETRIX (Santa Clara, Calif.), Polymorphism chipsgap-LCR (Abravaya et al. Nucl Acids Res 23:675-682 (1995)), and radioactive and/or fluorescent DNA sequencing using standard procedures well known in the art.

In one embodiment, amplification of genomic DNA for use in testing for an OSD mutation is performed by PCR. For this embodiment, PCR primers and a method of using the primers in amplification reactions are provided such that different amplification products are observed when DNA is amplified from affected, drd1 mutation carrier or drd2 mutation carrier, or normal dogs. It will be recognized by those skilled in the art that while particular sequences of PCR primers are provided herein, other PCR primer sequences can be designed to detect the presence or absence of an OSD mutation.

When PCR primers are used such that the amplification products are of distinct sizes, the amplification products can be analyzed by standard methods such as electrophoretic separation and detection using ethidium bromide and ultraviolet light, or any other suitable detection method. Alternatively, amplification products can be isolated and sequenced using any of a variety of techniques.

The method of the present invention can be carried out for any breed of dog. In general, dogs known to be affected with OSD include Labrador retrievers and Samoyeds. However, any other breed of dog, including mixed breeds, may be tested according to the method of the invention. Some non-limiting examples of dog breeds that could be tested in the method of the invention include Akita, American cocker spaniel, American eskimos, Australian cattle dog, Australian stumpy tailed cattle dog, basenji, Bernese mountain dog, border collie, Chesapeake bay retriever, Chinese crested, English cocker spaniel, English mastiff, English springer spaniel, Entlebucher mountain dog, Finnish lapphund, German shorthaired pointer, giant schnauzer, Havanese, lowchen, miniature poodle, miniature schnauzer, Nova scotia duck tolling retriever, Portuguese water dogs, silky terrier, spitz, standard poodle, standard wirehaired dachshund, Tibetan terriers and toy poodle.

Also provided in the present invention are kits for detecting the presence or absence of an OSD mutation in a biological sample from a dog or a nucleic acid sample extracted from the biological sample. The kits of the present invention comprise reagents for nucleic acid based detection of the presence of an OSD mutation. In one embodiment, the kits comprise reagents for extraction/preparation of nucleic acid samples and pair(s) of specific primers for identification of OSD mutations.

The presently provided OSD mutation tests will allow diagnosis of dogs of any age, such as a fetal dog (in utero), neonatal dogs, adult dogs, etc., and will eliminate the false positives and false negatives that have complicated previous identification of the OSD status of dogs. Accordingly, by using the tools and method described herein, dogs which are genetically OSD normal, drd1 mutation carriers or drd2 mutation carriers, or dogs affected with OSD, can be identified and selected for breeding. It is preferable to select dogs that are normal for OSD for mating. However, the method also permits removal of carrier or affected dogs from a breeding stock. Alternatively, dogs which are heterozygous for an OSD mutation can be mated with genetically normal dogs to ensure the absence of dogs affected with OSD in the litter.

The invention will be further understood by the following examples, which are intended to be illustrative and not restrictive in any way.

EXAMPLE 1

This Example illustrates discovery of the drd2 mutation and presents particular embodiments of the invention that are useful for detecting the presence or absence of the drd2 mutation.

The CanFam2 May 2005 dog whole genome shotgun assembly v2.0 (available at genome.ucsc.edu/cgi-bin/hg-Gateway) identifies 30 predicted exons of the canine homolog of the human COL9A2 gene, but fails to predict homologs of human exons 1 and 26. The earlier (July 2004) CanFam1 assembly does identify a predicted canine exon 1 homolog, but comparisons between the 2004 (CanFam1) and 2005 (CanFam2) assemblies identified sequence inconsistencies between them in the interval corresponding to the 5' end, exon 1 and part of intron 1 of the predicted canine COL9A2 gene.

We designed primers based on the 2004 assembly to amplify overlapping cDNA fragments to cover the complete coding sequence of the canine COL9A2 by RT-PCR (Table 1).

Shown in Table 1 are primer sequences used to amplify the complete coding region of COL9A2 (primer pairs 1 to 10), as well as to amplify COL9A3 (primer pairs 11 to 21). Also shown are the sequences of primer pairs used to retrieve the correct 5' end sequence of the Col9A2 gene. The primers were used to amplify cDNA from retina samples obtained from normal dogs, and dogs homozygous for the drd2 mutation which were therefore affected with OSD. These normal and affected dogs were members of a controlled breeding colony we established. Briefly, the colony was established from a purebred Samoyed affected with OSD (a dog that was homozygous for the drd2 mutation). This dog was bred to homozygous normal Irish-setter dogs and the heterozygous F1 progeny were then backcrossed to dogs homozygous for the drd2 mutation (affecteds) or intercrossed to drd2 mutation carriers to yield litters segregating the drd2 phenotype. Five related three-generation families from this colony (two intercrosses and three backcrosses), which included 63 progeny, were studied.

TABLE 1

| Pair | Forward primer name | Forward primer sequence | Reverse primer name | Reverse primer sequence |
|---|---|---|---|---|
| A. Col9A2 primers used to amplify the coding sequence. | | | | |
| 1 | COL9A2_5UTR_F4 | ccgccccgtccgagagcagc (SEQ ID NO: 8) | COL9A2exon4R | gcttcccatcaggcccatctgg (SEQ ID NO: 9) |
| 2 | COL9A2exon1F | gagcctccgccgcccgcatg (SEQ ID NO: 10) | COL9A2exon4_5R | gctccagttagaccatcaatcc (SEQ ID NO: 11) |
| 3 | COL9A2rg1F (exon1_2) | ctggcgcagatcagaggt (SEQ ID NO: 12) | COL9A2rg1R (exon10_11) | cagttggtcggacacaagaa (SEQ ID NO: 13) |
| 4 | COL9A2exon2F | cctggatccgacggcatcgac (SEQ ID NO: 14) | COL9A2exon7_8R | gtggtccaggaggtccagcaaag (SEQ ID NO: 15) |
| 5 | COL9A2exon4_5F | tgggattgatggtctaactgg (SEQ ID NO: 16) | COL9A2exon22R | gggtccgatttctccttgag (SEQ ID NO: 17) |
| 6 | COL9A2exon21F | ctccctggattctctggtcc (SEQ ID NO: 18) | COL9A2exon26R | gcccttctcgcctttctctc (SEQ ID NO: 19) |
| 7 | COL9A2exon24F | cttgccaggcatcaagggagac (SEQ ID NO: 20) | COL9A2exon31R | ggtcaccctcctctccacgtttt (SEQ ID NO: 21) |

TABLE 1-continued

| Pair | Forward primer name | Forward primer sequence | Reverse primer name | Reverse primer sequence |
|---|---|---|---|---|
| 8 | COL9A2exon24_25F | atcaagggagacaagggcttcc (SEQ ID NO: 22) | COL9A2exon30R2 | ctcacagcgacctctgccagt (SEQ ID NO: 23) |
| 9 | COL9A2exon29F | cgaccagcacatcgtgaccgt (SEQ ID NO: 24) | COL9A2exon32R | tccttgccgttgattgcctg (SEQ ID NO: 25) |
| 10 | COL9A2exon30_31F2 | ccaagggaaaacgtggagagaag (SEQ ID NO: 26) | ColA2_3UTR_R2 | gaaagctggcttcctggtctgag (SEQ ID NO: 27) |

B. Col9A3 primers used to amplify the coding sequence.

| Pair | Forward primer name | Forward primer sequence | Reverse primer name | Reverse primer sequence |
|---|---|---|---|---|
| 11 | COL9A3_5UTR_F | gcgcgcagagccgctgagag (SEQ ID NO: 28) | COL9A3exon8R | attccaccggggacaccact (SEQ ID NO: 29) |
| 12 | | | COL9A3rg1R (exon10) | ggaggacccctgggtgac (SEQ ID NO: 30) |
| 13 | | | COL9A3exon12R2 | cgacctctccttgatctcctt (SEQ ID NO: 31) |
| 14 | COL9A3rg1F (exon12) | gcagaaagtgggacctcaag (SEQ ID NO: 32) | COL9A3exon8R | attccaccggggacaccact (SEQ ID NO: 29) |
| 15 | | | COL9A3rg1R (exon10) | ggaggacccctgggtgac (SEQ ID NO: 30) |
| 16 | COL9A3exon4F | aagccagggaagccaggaga (SEQ ID NO: 33) | COL9A3exon8R | attccaccggggacaccact (SEQ ID NO: 29) |
| 17 | | | COL9A3rg1R (exon10) | ggaggacccctgggtgac (SEQ ID NO: 30) |
| 18 | COL9A3exon8F | agaggcaggagagagtggtgt (SEQ ID NO: 34) | COL9A3exon12R | cttgccgacctctccttgat (SEQ ID NO: 35) |
| 19 | | | COL9A3exon25_26R | aacgccctggtctcccttag (SEQ ID NO: 36) |
| 20 | COL9A3exon20_21F | gaagggagaactgctggagag (SEQ ID NO: 37) | COL9A3exon29_30R | gatttgttcgctgagcatcc (SEQ ID NO: 38) |
| 21 | COL9A3exon26F | ctggggacaaaggagagctg (SEQ ID NO: 39) | COL9A3_3UTR_R2 | cccgaggtacgatgttagagc (SEQ ID NO: 40) |

C. Col9A2 primers used to amplify genomic DNA.

| Pair | Forward primer name | Forward primer sequence | Reverse primer name | Reverse primer sequence |
|---|---|---|---|---|
| 22 | Col9A2_5UTR_F2 | tgtggtaggctttcctgaaga (SEQ ID NO: 41) | A2i2R2 | cccgacccaggttagagact (SEQ ID NO: 42) |
| 23 | Col9A2_5UTR_F3 | aaaagcctgacctcctagctg (SEQ ID NO: 43) | | |
| 24 | Col9A2_5UTR_F7 | ccggttctgtgctgctaagccag (SEQ ID NO: 44) | | |
| 25 | A2_exon1_F | gagcctccgccgccccgcatg (SEQ ID NO: 45) | A2int1R11 | cgcctaacccgaaaggagcac (SEQ ID NO: 46) |
| 26 | A2_exon1_F2 | ctgctgctgctccaggggctc (SEQ ID NO: 47) | | |
| 27 | A2_F11 | gcccggttctgtgctgctaag (SEQ ID NO: 48) | | |
| 28 | A2_exon1_F2 | ctgctgctgctccaggggctc (SEQ ID NO: 47) | A2int1R | gtgaatgggcaccattgtct (SEQ ID NO: 49) |
| 29 | A2_F10 | ccggttctgtgctgctaag (SEQ ID NO: 50) | A2int1R10 | cctaacccgaaaggagcac (SEQ ID NO: 51) |

Amplification of affected retina cDNA resulted in a lack of amplification product from PCR analysis using three primer pairs (primer pairs 1, 2 and 3 in table 1). This indicated that the genomic sequence at the 5' end of the gene in affected dogs is mutated, which results in a lack of amplification products. After retrieving the correct 5' end of the gene from a dog normal for OSD using primer pairs 22 to 29 in Table 1, a comparison of this region of COL9A2 to the drd2-affected (homozygous for the drd2 mutation) dog revealed a 1,267 bp deletion in the affected dog-(illustrated in FIGS. 1-3).

To identify dogs that were normal for OSD, that were drd2 mutation carriers, and that were affected with OSD via homozygosity for the drd2 mutation, as well as to analyze co-segregation of the COL9A2 mutation with the disease in the Samoyed derived colony dogs, genomic DNA of 70 Samoyed-colony-derived dogs were amplified using two primer pairs (primer pairs 1 and 2 in table 2). Analysis of the resulting PCR amplification products showed complete co-segregation with the disease: all affected dogs were homozygous for the drd2 mutation, all obligated carriers were heterozygous for the drd2 mutation, and all known normal dogs were homozygous for the wild type allele.

Thus, this Example demonstrates the discovery of the drd2 mutation and its association with OSD, and illustrates a method for detecting the presence or absence of this mutation in to ascertain the OSD status of dogs.

EXAMPLE 2

Based on our discovery of the drd2 mutation as set forth in Example 1, we designed another PCR based test. This test was performed on samples obtained from dogs obtained from the control colony described in Example 1. A pedigree for dogs analyzed in this Example is presented in FIG. 5A.

Figure 5B:
FIGS. 5B and 5C provide photographic representation of electrophoretic separation of PCR amplification products from drd2 COL9A2 tests performed on biological samples obtained from the dogs depicted in the pedigree.
Figure 5C:

The primers used in this Example are presented in Table 2 (primer pairs 1 and 2). The two primer pairs were used in separate PCR reactions (Table 2). Representative PCR amplification products obtained using primer pair 1 are shown in FIG. 5B. Representative PCR amplification products obtained using primer pair 2 are shown in FIG. 5C.

To obtain the PCR results presented in FIGS. 5B and 5C, 50-100 ng of genomic DNA were mixed with 12.5 ul of GoTaq green master mix (Promega, Catalog number M7123), 1.25 ul of DMSO (5% final concentration) and 10 uM of forward and reverse primers in a final volume of 25 ul. The DNA was then denatured at 95° C. for 2 minutes and 35 cycles of 95° C. for 30 seconds, 58° C. (for primer pair number 1) or 60° C. (for primer pair number 2) for 30 seconds, 72° C. for 30 seconds were performed in a thermal cycler (MJ Research, Watertown, Mass., USA). An additional final extension of 5 minutes at 72° C. was performed to ensure full-length products.

Primer pair number 1 in Table 2 produces a 1,445 bp product from amplification of wild type (normal) chromosomes while a smaller molecular weight product (178 bp) is observed from amplification of affected chromosomes (FIG. 5B). Since in carrier dogs both alleles are present, this PCR reaction will usually produce only the smaller molecular weight product in carriers due to competition between the targets and the differences in size between the two amplicons. Therefore, a second PCR reaction can be performed using primer pair number 2 in Table 2. This primer pair yields a 504 bp product from amplification of wild type (normal) chromosomes and will not result in any product from affected chromosomes because the binding site for the reverse primer is located within the deletion (FIG. 5C). PCR products obtained using this strategy to amplify DNA obtained from normal dogs, dogs that are drd2 mutation carriers, and dogs that were affected with OSD via homozygosity for drd2. The PCR products were visualized on a 1.8% agarose gel and stained with Ethidium Bromide using standard protocols. A normal dog yielded either a faint 1,445 bp band in the reaction using primer pair number 1 or no visible band and a 504 bp band from PCR amplification using primer pair 2 (FIG. 5A dog 13). A carrier dog yielded a 178 bp band from PCR amplification using primer pair 1 and a 504 bp band using primer pair 2 (FIG. 5A dogs 1,3,4,5,6,9,10,11,12). Amplification from an OSD affected dog (homozygous for the drd2 mutation) yields only a 178 bp band from PCR amplification using primer pair 1 and no amplification when using primer pair 2 (FIG. 5A, dogs 2,7,8).

TABLE 2

| | Primer Pairs | | | Expected Size | | |
|---|---|---|---|---|---|---|
| Forward primer # | Forward primer name | Forward primer sequence | Reverse primer name | Reverse primer sequence | Expected size in wt | Expected size in carrier | Expected size in affected |
| 1 | COL9A2_Part1_1F | gctgaccttgtggattttctcc SEQ ID NO: 52 | COL9A2intron1R | gtgaatgggcaccattgtct SEQ ID NO: 53 | 1,445 bp | 178 bp | 178 bp |
| 2 | COL9A2_Part10F | catctctccctcactccctcct SEQ ID NO: 54 | COL9A2_Part10R | tcacccctctcccagtctcttag SEQ ID NO: 55 | 504 bp | 504 bp | No band |
| 3 | COL9A3test1F | gctgccactgggctcctttcttcg SEQ ID NO: 56 | COL9A3test1R | agcaggagcagggccagcgtg SEQ ID NO: 57 | 248 bp | 248 bp and 249 bp | 249 bp |
| 4 | COL9A3test1F | gctgccactgggctccttttcttcg SEQ ID NO: 56 | COL9A3test1R3 | cgctcacatgcgccccggtc SEQ ID NO: 58 | 298 bp | 298 bp and 299 bp | 299 bp |
| 5 | COL9A3_AS_WF | ggcgcagccatggccgggac SEQ ID NO: 59 | COL9A3_AS_R | ggtcagggtggcgccaggagc SEQ ID NO: 60 | 72 bp | 72 bp | No band |
| 6 | COL9A3_AS_AF | ggcgcagccatggccgggcg SEQ ID NO: 61 | COL9A3_AS_R | ggtcagggtggcgccaggagc SEQ ID NO: 60 | No band | 73 bp | 73 bp |

Thus, this Example demonstrates an embodiment of the invention that is useful for determining OSD status by testing for the presence or absence of the COL9A2 drd2 mutation.

EXAMPLE 3

This Example demonstrates an embodiment of the invention using the PCR based method described in Example 2 to test unrelated Samoyeds (meaning the dogs had no parents or grandparents in common).

Fifty-five unrelated Samoyed dogs were screened for the presence or absence COL9A2 drd2 mutation using this test. One Samoyed was found to be a drd2 mutation carrier and is therefore considered to be a carrier of the drd2 form of OSD. Another 126 dogs, considered to be normal for OSD based on phenotypic analysis, from 26 additional breeds were screened for the deletion and all the dogs had the wild type (normal) genotype (Table 3).

TABLE 3

| Breed | Number of dogs | drd2 mutation Carriers |
|---|---|---|
| American Cocker Spaniel | 5 | 0 |
| American Eskimos | 10 | 0 |
| American Pitbull Terrier | 5 | 0 |
| American Staffordshire Terrier | 5 | 0 |
| Australian Cattle Dogs | 5 | 0 |
| Basenji | 1 | 0 |
| Border Collies | 5 | 0 |
| Boxer | 1 | 0 |
| Chesapeake Bay Retriever | 5 | 0 |
| Chinese Crested | 5 | 0 |
| English Cocker Spaniel | 5 | 0 |
| English Springer Spaniel | 7 | 0 |
| Entelbucher Mountain Dogs | 7 | 0 |
| Glen Of Immal Terrier | 6 | 0 |
| Golden Retriever | 5 | 0 |
| Golden Retriever/Labrador Retriever Crosses | 5 | 0 |
| Labrador Retriever | 5 | 0 |
| Nova Scotia Duck Tolling Retriever | 4 | 0 |
| Samoyed | 55 | 1 |
| Papillon | 7 | 0 |
| Poodle | 7 | 0 |
| Portuguese Water Dogs | 5 | 0 |
| Tibetan Terrier | 8 | 0 |
| American Bulldog | 2 | 0 |
| Pomeranian | 1 | 0 |
| Corgi | 4 | 0 |
| Dachshund | 1 | 0 |
| Total | 181 | 1 |

Thus, this Example demonstrates another embodiment of the invention that is useful for determining OSD status in dogs by testing for the presence or absence of the drd2 mutation.

EXAMPLE 4

This Example describes discovery of the drd1 mutation and particular embodiments of methods for testing for the presence or absence of this mutation.

Our comparison of the 2005 CanFam2 dog sequence assembly to the human COL9A3 genomic sequence identified 29 predicted canine exons and failed to identify predicted exons homologous to human exons 16, 17 and 32. Based on this analysis, 12 primers (Table 1 primer pairs 11 to 21) were designed to amplify overlapping cDNAs obtained from one normal, and one affected dogs derived from Labrador retriever colony dogs to cover the complete coding region of the canine Col9A3. Briefly, the Labrador retriever colony dogs are descended from two unrelated purebred Labrador retrievers affected with OSD. These dogs were bred to homozygous normal unrelated Beagles, Beagle-crossbred dogs, Irish-Setter and Irish-setter-crossbreds dogs and poodle-crossbred dogs, and the heterozygous F1 progeny were then backcrossed to affected dogs or intercrossed to carriers of the drd1 mutation to yield litters segregating the OSD phenotype. Eight related three-generation families from this colony (five intercrosses and three backcrosses), which included 68 progeny, were analyzed using 12 primers were in 11 different combinations of primer pairs to produce redundant overlapping fragments.

Our comparison of retinal cDNA amplification products from normal dogs and dogs homozygous for the drd1 mutation revealed a one-base insertion (guanine) in the coding sequence (exon 1) that changes a string of 4 guanines (nucleotides 49,699,847-49,699,850 of canine chromosome 24 in the May 2005 CanFam2 assembly v2.0; <genome.ucsc.edu/cgi-bin/hgGateway>) to a string of 5 Gs. This mutation is indicated by the presence of the G at nucleotide position 11 in the nucleotide sequence depicted in FIG. 4B (SEQ ID NO:4). The string of five Gs is as depicted in FIG. 4B for nucleotides 7-11.

To identify drd1-affected (homozygous for the drd1 mutation), drd1 mutation carrier and normal dogs in the Labrador retriever derived colony, and to analyze co-segregation of the drd1 mutation with the disease, genomic DNA of 80 colony dogs was amplified using the primer pairs COL9A3test1F and COL9A3test1R (Table 2, primer pair 3). Sequencing of the 248 bp amplicon with the forward primer identified normal animals (4 Gs) or affected animals (5 G's, 249 bp amplicon) while an overlapping chromatogram was observed in carrier dogs at the insertion point. All outbred normal dogs were determined to be homozygous wild type. All affected dogs were determined to be homozygous for the drd1 mutation (5 Gs). All the obligated carriers were determined to be heterozygous for the drd1 mutation (overlapping chromatograms; not shown). 30 unaffected dogs from intercrosses were genotyped as follows: 5 were homozygous normal (4 Gs) and 25 were heterozygoug for the drd1 mutation. These results accordingly showed a complete co-segregation of the drd1 mutation with the disease in the colony.

In another test, we employed the primer pair COL9A3test1F and COL9A3test1R3 (Table 2, primer pair 4). Sequencing of the 298 bp product with the forward and the reverse primers identified normal sequence or affected sequence (299 bp) while an overlapping chromatogram was observed in drd1 mutation carrier dogs after the insertion point (sequencing data not shown).

Thus, this Example demonstrates the discovery of the drd1 mutation and its association with OSD, and illustrates a method for detecting the presence or absence of this mutation to determine the OSD status of dogs.

EXAMPLE 5

This Example describes another embodiment by which the presence or absence of the drd1 mutation can be determined. In particular, we designed an allele-specific PCR based test using primer pairs 5 and 6 presented in Table 2, namely: Forward (wild type primer): 5'-GGCGCAGCCATGGC-CGGGAC-3' (COL9A3_AS_WF; SEQ ID NO:59); Forward (mutant primer): 5'-GGCGCAGCCATGGCCGGGCG-3' (COL9A3_AS_AF; SEQ ID NO:61); and Reverse primer: 5'-GGTCAGGGTGGCGGCCAGGAGC-3' (COL9A3_AS_R; SEQ ID NO:60).

Figure 6:
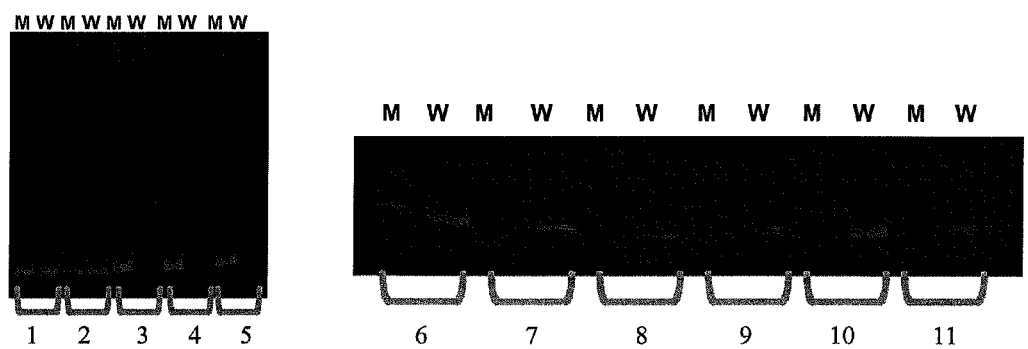
FIG. 6 provides a photographical representation of electrophoretic separation of PCR amplification products from drd1 COL9A3 tests.

DNA samples were obtained from normal, drd1 mutation carrier and affected dogs from our control colony of Labrador retrievers. Each DNA sample was analyzed in separate PCR reactions, with primer pairs 5 (wild type forward and reverse primers) and 6 (mutant forward primer and wild type reverse primer). The reactions were performed in a total volume of 15 µl, containing 1×PCR buffer (Qiagen); 10-100 ng/µl total DNA; 0.3 µM forward (wild or mutant type) and reverse primers; 0.2 mM each of four dNTPs; 1.5 mM MgCl2; 17% DMSO and 0.375 units Taq-polymerase. The reaction mixture was overlaid with mineral oil. The enzyme Taq-pol (5 u/µl) is diluted 1:10 with water and 0.75 µl was added to the reaction in a "hot-start" manner: the enzyme was added after the denaturing step at 94C). The PCR cycles were: 1 cycle of 94C for 3 minutes; 32 cycles of 94C for 15 seconds, 58C for 30 seconds and 72C for 15 seconds. From each PCR amplification, 6-8 µl was analyzed by electrophoresis on a 6% PAGE in TBE buffer with ~1 mg/ml of ethidium bromide for staining. Representative photographs of electrophoretic separation of amplification products obtained from using this protocol are presented in FIG. 6, where M=mutant PCR (primer pair 6), W=Wild type PCR (primer pair 5). Samples 1, 2 and 6 are drd1 mutation carriers and are therefore considered carriers of the drd1 form of OSD, samples 3, 4 and 5 are affected with OSD, and samples 7, 8, 9, 10, and 11 are normal for OSD. The sizes of the amplification products are provided in Table 2.

Thus, this Example demonstrates another embodiment of the invention that is useful for determining OSD status in dogs by testing for the presence or absence of the drd1 mutation.

EXAMPLE 6

This Example provides an illustration of determining the presence or absence of the drd1 mutation in unrelated dogs to determine OSD status.

In particular, 59 phenotypically normal unrelated Labrador retrievers (no parents or grandparents in common), and 19 unrelated Labrador retrievers with retinal folds were tested for the presence or absence of the drd1 mutation. One dog with retinal folds was found to be homozygous for the mutation (affected). 78 dogs considered normal for OSD via phenotypic examination from 23 additional breeds were also screened and all 78 dogs were normal for the mutation (Table 4), meaning they were homozygous wild type for the drd1 gene.

TABLE 4

| Breed | Number of dogs | drd1 mutation carriers | Affected (homozygous for the drd1 mutation) |
|---|---|---|---|
| American cocker spaniel | 2 | 0 | 0 |
| American Eskimos | 3 | 0 | 0 |
| Australian cattle dogs | 6 | 0 | 0 |
| Basenji | 2 | 0 | 0 |
| Border Collies | 10 | 0 | 0 |
| Boxer | 1 | 0 | 0 |
| Chesapeake bay retriever | 4 | 0 | 0 |
| Chinese crested | 4 | 0 | 0 |
| Collie | 5 | 0 | 0 |
| English cocker spaniel | 8 | 0 | 0 |
| Entelbucher mountain dogs | 1 | 0 | 0 |
| Glen of Immal terrier | 2 | 0 | 0 |
| Golden Retriever | 4 | 0 | 0 |
| Irish Setter | 1 | 0 | 0 |
| Labrador retrievers | 78 | 0 | 1 |
| mix | 6 | 0 | 0 |
| Nova scotia duck tolling retriever | 4 | 0 | 0 |
| Poodle | 3 | 0 | 0 |
| Portuguese water dogs | 4 | 0 | 0 |
| American Bulldog | 2 | 0 | 0 |
| Pomeranian | 1 | 0 | 0 |
| Corgi | 4 | 0 | 0 |
| Dachshund | 1 | 0 | 0 |
| Total | 156 | 0 | 1 |

Thus, this Example demonstrates yet another embodiment of the invention that is useful for determining OSD status by testing for the presence or absence of the drd1 mutation.

The invention has been described through specific embodiments. However, routine modifications to the compositions, methods and devices will be apparent to those skilled in the art and such modifications are intended to be covered within the scope of the invention.

We claim:

1. A method for determining whether a dog is heterozygous, homozygous or has an absence of a drd1 mutation identified as a G in position 11 as depicted in nucleotide sequence of SEQ ID NO:4 (mutation 1), and/or whether the dog is heterozygous, homozygous or has an absence of a drd2 mutation identified as a deletion of 1,267 nucleotides between nucleotide number 230 and nucleotide number 1,498 in nucleotide sequence of SEQ ID NO:2 (mutation 2), the method comprising: obtaining a biological sample from the dog determining the presence or absence of the drd1 or drd2 mutation and from the biological sample identifying the dog as:

drd1 mutation homozygous by determining homozygosity for mutation 1; or drd1 mutation heterozygous by determining heterozygosity for mutation 1; or drd1 mutation absent based by determining an absence of mutation 1; or drd2 mutation homozygous by determining homozygosity for mutation 2; or drd2 mutation heterozygous by determining heterozygosity for mutation 2; or drd2 mutation absent based by determining an absence of mutation 2.

2. The method of claim 1, wherein identification of the G in position 11 is carried out by determining the presence of 5 consecutive Gs in SEQ ID NO:4 starting at position 7.

3. The method of claim 1, wherein the mutation 1 or the mutation 2 is detected by analysis of polymerase chain reaction amplification product.

4. The method of claim 1, wherein the dog is a breed of dog selected from the group of dog breeds consisting of Akita, American cocker spaniel, American eskimos, Australian cattle dog, Australian stumpy tailed cattle dog, basenji, Bernese mountain dog, border collie, Chesapeake bay retriever, Chinese crested, English cocker spaniel, Samoyed, English mastiff, English springer spaniel, Entlebucher mountain dog, Finnish lapphund, Labrador retriever, German shorthaired pointer, giant schnauzer, Havanese, lowchen, miniature poodle, miniature schnauzer, Nova scotia duck tolling retriever, Portuguese water dogs, silky terrier, spitz, standard poodle, standard wirehaired dachshund, Tibetan terriers and toy poodle.

5. The method of claim 1, wherein the biological sample is selected from the group consisting of blood, hair, mucosal scrapings, semen, tissue biopsy and saliva.

6. The method of claim 5, wherein the biological sample is collected from a fetal dog, a neonatal dog, or an adult dog.

7. The method of claim 1, further comprising selecting a dog for breeding, wherein a dog selected for breeding exhibits an absence of mutation 1 and mutation 2, or is heterozygous for mutation 1 or mutation 2 and is selected for breeding with a dog that exhibits an absence of mutation 1 and mutation 2.

8. The method of claim 1, further comprising communicating to an individual a result obtained from determining the presence or absence of mutation 1 and/or mutation 2.

9. A method for determining whether a Laborador retriever is a carrier for drd1 form of Oculo-skeletal dysplasia (OSD) or is affected with OSD comprising the steps of obtaining a biological sample from the Laborador retriever and determining from the biological sample the presence of a G in position 11 of the nucleotide sequence depicted in SEQ ID NO:4, and
identifying the Laborador retriever as a carrier of drd1 form of OSD based on heterozygosity for the presence of the G in position 11 of the nucleotide sequence depicted in SEQ ID NO:4, or identifying the Laborador retriever as affected with OSO based on homozygosity for the presence of the G in position 11 of the nucleotide sequence of SEQ ID NO:4.

10. The method of claim 9 wherein upon determination of heterozygosity for the presence of the G in position 11 of the nucleotide sequence depicted in SEQ ID NO:4, a further step of determination of status of drd2 form of OSD is carried out.

11. The method of claim 10, wherein the status of drd2 form of OSD is determined by detecting the presence or absence of a deletion of 1,267 nucleotides between nucleotide number 230 and nucleotide number 1,498 of nucleotide sequence of SEQ ID NO:2.

12. The method of claim 9, wherein determining the presence of the G in position 11 of the nucleotide sequence as depicted in SEQ ID NO:4 comprises determining 5 consecutive Gs starting at position 7 of SEQ ID NO:4.

13. The method of claim 9, wherein determining the presence of the G in position 11 of the nucleotide sequence as depicted in SEQ ID NO:4 is carried out by polymerase chain reaction.

14. A method for determining whether a Samoyed is a carrier for drd2 form of Oculo-skeletal dysplasia (OSD) or is affected with OSD comprising the steps of obtaining a biological sample from the Samoyed and determining from the biological sample the presence of a deletion of 1,267 nucleotides between nucleotide number 230 and nucleotide number 1,498 of the nucleotide sequence as depicted in SEQ ID NO:2; and
identifying the Samoyed as a carrier of drd2 form of OSD based on heterozygosity for the presence of the deletion or identifying the Samoyed as affected with OSO based on homozygosity for the presence of the deletion.

15. The method of claim 14, wherein the presence or absence of the deletion is detected by analysis of polymerase chain reaction amplification product.

16. The method of claim 14 wherein upon identification of the deletion, a further step of determination of status of drd1 form of OSD is carried out.

17. The method of claim 16, wherein the status of drd1 form of OSD is determined by detecting the presence or absence of a G in position 11 of the nucleotide sequence depicted in SEQ ID NO:4.

\* \* \* \* \*